US006410701B1

(12) United States Patent
Soppet et al.

(10) Patent No.: US 6,410,701 B1
(45) Date of Patent: *Jun. 25, 2002

(54) HUMAN NEUROPEPTIDE RECEPTOR

(75) Inventors: Daniel R. Soppet, Centreville, VA (US); Yi Li, Gaithersburg; Craig A. Rosen, Laytonsville, both of MD (US)

(73) Assignee: Human Genome Sciences, Inc., Rockville, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/462,509

(22) Filed: Jun. 5, 1995

(30) Foreign Application Priority Data

May 5, 1995 (WO) ................................ PCT/US95/05616

(51) Int. Cl.[7] ........................ C07H 21/02; C07H 21/04; C12P 1/00; C12P 21/06
(52) U.S. Cl. ..................... 536/23.1; 536/23.4; 536/23.5; 536/24.3; 536/24.5; 435/41; 435/69.1; 435/69.7; 435/70.1
(58) Field of Search ...................... 435/41, 69.1, 69.7, 435/70.1, 70.3, 71.1, 71.2, 89, 91.1, 91.4, 325, 361, 252.3, 320.1; 536/23.1, 23.4, 23.5, 24.3, 24.5

(56) References Cited

U.S. PATENT DOCUMENTS

| | | | |
|---|---|---|---|
| 5,527,676 A | * | 6/1996 | Vogelstein et al. |
| 5,935,814 A | | 8/1999 | Bergsma et al. |
| 6,020,157 A | | 2/2000 | Bergsma et al. |

FOREIGN PATENT DOCUMENTS

| | | | |
|---|---|---|---|
| EP | 0121352 | * | 10/1984 |
| EP | 0875566 | | 10/1997 |
| EP | 0875565 | | 11/1998 |
| WO | 9309277 | | 5/1993 |
| WO | WO 93/09277 | | 5/1993 |
| WO | 93/11249 | * | 6/1993 |
| WO | 9405695 | | 3/1994 |
| WO | WO 94/05695 | | 3/1994 |
| WO | 9605302 | | 2/1996 |
| WO | WO96/34877 | | 11/1996 |

OTHER PUBLICATIONS

ATCC Catalogue of Cell Lines & Hybridomas, 7th edition, 1992.*
Mills et al, Trends in Pharmacological Sciences, 14(11):394–396, 1993.*
Herzog et al, DNA and Cell Biology, 12(6):465–471, 1993.*
Jazin et al., Regulatory Peptides, 47:247–258, 1993.*
Lebo et al, Cold Spring Harbor Symp. Quant. Biol., 51:169–176, 1956.*
Luttrell et al., Science, vol. 259:1453–1457 (1993).
Probst et al., DNA and Cell Biology, vol. 11:1–20 (1992).
de Weerth et al., Biochem. Biophys. Res. Comm., vol. 194:811–818 (1993).
Sakurai et al., Cell, vol. 92:573–585 (1998).
Yan et al., PNAS, vol. 93:4661–4665 (1996).
Leibel et al., Crit. Rev. Food Sci. and Nutr., vol. 33:351–358 (1993).
Hawes et al., J. Biol. Chem., vol. 269:15776–15785 (1994).
Tartaglia et al., Cell, vol. 83:1263–1271 (1995).
Mantzoros et al., Diabetes, vol. 45:909–914 (1996).
Lundell et al., PNAS, vol. 93:5111–5115 (1996).
Gehlert et al., Mol. Pharmacol., vol. 49:224–228 (1996).
Genbank Accession No.: R40951 (May 22, 1995).
Genbank Accession No.: R55705 (May 22, 1995).
Genbank Accession No.: JN0692 (Feb. 23, 1997).
GeneSeq Accession No.: T51065 (Mar 13, 1997).
GeneSeq Accession No.: T13909 (Aug. 27, 1996).
Genbank Accession No.: R55704 (May 22, 1995).
GeneSeq Accession No.: R91233 (Aug. 27, 1996).
GeneSeq Accession No.: W11236 (Mar. 13, 1997).
FASEB Journal 8:72–80 (1994).
TINS, 17:373–379 (1994).
Nature 372:425–432 (1994).
Nature 372:406–407 (1994).
Herzog et al. (1993) J. Biol. Chem. 268(9):6703–6707.
PCT International Search Report. Issued Jul. 31, 1995.
International Search Report, Application No. PCT/US00/24518, dated Jan. 18, 2001.
FASEB Journal, vol. 8, pp. 72–80, (Jan. 1994).
TINS, vol. 17, No. 9, pp. 373–379, (1994).
Nature, vol. 372, pp. 425–432, (Dec. 1, 1994).
Nature, vol. 372, pp. 406 and 407, (Dec. 1, 1994).

* cited by examiner

Primary Examiner—L. F. Smith
(74) Attorney, Agent, or Firm—Human Genome Sciences, Inc.

(57) ABSTRACT

Human neuropeptide receptor polypeptides and DNA (RNA) encoding such polypeptides and a procedure for producing such polypeptides by recombinant techniques is disclosed. Also disclosed are methods for utilizing such polypeptides for identifying antagonists and agonists to such polypeptides and methods of using the agonists and antagonists therapeutically to treat conditions related to the underexpression and overexpression of the neuropeptide receptor polypeptides, respectively. Also disclosed are diagnostic methods for detecting a mutation in the neuropeptide receptor nucleic acid sequences and an altered level of the soluble form of the receptors.

169 Claims, 10 Drawing Sheets

```
  1 ATGGAGCCCT CAGCCACCCC AGGGGCCCAG ATGGGGGTCC  40
  1  M   E   P   S   A   T   P   G   A   Q   M   G   V    14

41 CCCCTGGCAG CAGAGAGCCG TCCCCTGTGC CTCCAGACTA  80
 14  P   P   G   S   R   E   P   S   P   V   P   P   D   Y  27

81 TGAAGATGAG TTTCTCCGCT ATCTGTGGCG TGATTATCTG 120
 27   E   D   E   F   L   R   Y   L   W   R   D   Y   L   40

121 TACCCAAAAC AGTATGAGTG GGTCCTCATC GCAGCCTATG 160
 41  Y   P   K   Q   Y   E   W   V   L   I   A   A   Y    54

161 TGGCTGTGTT CGTCGTGGCC CTGGTGGGCA ACACGCTGGT 200
 54  V   A   V   F   V   V   A   L   V   G   N   T   L   V  67

201 CTGCCTGGCC GTGTGGCGGA ACCACCACAT GAGGACAGTC 240
 67   C   L   A   V   W   R   N   H   H   M   R   T   V   80

241 ACCAACTACT TCATTGTCAA CCTGTCCCTG GCTGACGTTC 280
 81   T   N   Y   F   I   V   N   L   S   L   A   D   V    94

281 TGGTGACTGC TATCTGCCTG CCGGCCAGCC TGCTGGTGGA 320
 94  L   V   T   A   I   C   L   P   A   S   L   L   V   D 107

321 CATCACTGAG TCCTGGCTGT TCGGCCATGC CCTCTGCAAG 360
107   I   T   E   S   W   L   F   G   H   A   L   C   K   120

361 GTCATCCCCT ATCTACAGGC TGTGTCCGTG TCAGTGGCAG 400
121  V   I   P   Y   L   Q   A   V   S   V   S   V   A    134

401 TGCTAACTCT CAGCTTCATC GCCCTGGACC GCTGGTATGC 440
134 V  L   T   L   S   F   I   A   L   D   R   W   Y   A 147

441 CATCTGCCAC CCACTATTGT TCAAGAGCAC AGCCCGGCGG 480
147   I   C   H   P   L   L   F   K   S   T   A   R   R  160

481 GCCCGTGGCT CCATCCTGGG CATCTGGGCT GTGTCGCTGG 520
161  A   R   G   S   I   L   G   I   W   A   V   S   L    174

521 CCATCATGGT GCCCCAGGCT GCAGTCATGG AATGCAGCAG 560
174 A  I   M   V   P   Q   A   A   V   M   E   C   S   S 187

561 TGTGCTGCCT GAGCTAGCCA ACCGCACACG GCTCTTCTCA 600
187   V   L   P   E   L   A   N   R   T   R   L   F   S   200

601 GTCTGTGATG AACGCTGGGC AGATGACCTC TATCCCAAGA 640
201   V   C   D   E   R   W   A   D   D   L   Y   P   K   214
```

FIG. 1A

```
641 TCTACCACAG TTGCTTCTTT ATTGTCACCT ACCTGGCCCC 680
214  I  Y  H  S   C  F  F   I  V  T   Y  L  A  P  227

681 ACTGGCCTC ATGGCCATGG CCTATTTCCA GATATTCCGC 720
227  L  G  L   M  A  M   A  Y  F  Q   I  F  R  240

721 AAGCTCTGGG GCCGCCAGAT CCCCGGCACC ACCTCAGCAC 760
241  K  L  W   G  R  Q  I   P  G  T   T  S  A  254

761 TGGTGCGGAA CTGGAAGCGC CCCTCAGACC AGCTGGGGGA 800
254 L  V  R  N   W  K  R   P  S  D   Q  L  G  D 267

801 CCTGGAGCAG GGCCTGAGTG GAGAGCCCCA GCCCCGGGGC 840
267  L  E  Q   G  L  S   G  E  P  Q   P  R  G  280

841 CGCGCCTTCC TGGCTGAAGT GAAGCAGATG CGTGCACGGA 880
281  R  A  F   L  A  E  V   K  Q  M   R  A  R  294

881 GGAAGACAGC CAAGATGCTG ATGGTGGTGC TGCTGGTCTT 920
294 R  K  T  A   K  M  L   M  V  V   L  L  V  F 307

921 CGCCCTCTGC TACCTGCCCA TCAGCGTCCT CAATGTCCTT 960
307  A  L  C   Y  L  P   I  S  V  L   N  V  L  320

961 AAGAGGGTGT TCGGGATGTT CCGCCAAGCC AGTGACCGCG 1000
321  K  R  V   F  G  M  F   R  Q  A   S  D  R  334

1001 AAGCTGTCTA CGCCTGCTTC ACCTTCTCCC ACTGGCTGGT 1040
334 E  A  V  Y   A  C  F   T  F  S   H  W  L  V 347

1041 GTACGCCAAC AGCGCTGCCA ACCCCATCAT CTACAACTTC 1080
347  Y  A  N   S  A  A   N  P  I  I   Y  N  F  360

1081 CTCAGTGGCA AATTCCGGGA GCAGTTTAAG GCTGCCTTCT 1120
361  L  S  G   K  F  R  E   Q  F  K   A  A  F  374

1121 CCTGCTGCCT GCCTGGCCTG GGTCCCTGCG GCTCTCTGAA 1160
374 S  C  C  L   P  G  L   G  P  C   G  S  L  K 387

1161 GGCCCCTAGT CCCCGCTCCT CTGCCAGCCA CAAGTCCTTG 1200
387  A  P  S   P  R  S   S  A  S  H   K  S  L  400

1201 TCCTTGTAG 1209
401  S  L  *  402
```

FIG. 1B

```
  1 ATGGAGCCCT CAGCCACCCC AGGGGCCCAG ATGGGGGTCC  40
  1  M  E  P   S  A  T  P   G  A  Q    M  G  V   14

41 CCCCTGGCAG CAGAGAGCCG TCCCCTGTGC CTCCAGACTA  80
 14  P  P  G   S  R  E  P   S  P  V    P  P  D  Y 27

81 TGAAGATGAG TTTCTCCGCT ATCTGTGGCG TGATTATCTG 120
 27  E  D  E    F  L  R    Y  L  W  R   D  Y  L  40

121 TACCCAAAAC AGTATGAGTG GGTCCTCATC GCAGCCTATG 160
 41  Y  P  K   Q  Y  E  W   V  L  I    A  A  Y   54

161 TGGCTGTGTT CGTCGTGGCC CTGGTGGGCA ACACGCTGGT 200
 54  V  A  V  F   V  V  A   L  V  G   N  T  L  V 67

201 CTGCCTGGCC GTGTGGCGGA ACCACCACAT GAGGACAGTC 240
 67   C  L  A   V  W  R    N  H  H    M  R  T  V 80

241 ACCAACTACT TCATTGTCAA CCTGTCCCTG GCTGACGTTC 280
 81  T  N  Y    F  I  V  N   L  S  L    A  D  V  94

281 TGGTGACTGC TATCTGCCTG CCGGCCAGCC TGCTGGTGGA 320
 94 L  V  T  A   I  C  L    P  A  S    L  L  V  D 107

321 CATCACTGAG TCCTGGCTGT TCGGCCATGC CCTCTGCAAG 360
107  I  T  E    S  W  L    F  G  H  A   L  C  K  120

361 GTCATCCCCT ATCTACAGGC TGTGTCCGTG TCAGTGGCAG 400
121  V  I  P   Y  L  Q  A   V  S  V    S  V  A   134

401 TGCTAACTCT CAGCTTCATC GCCCTGGACC GCTGGTATGC 440
134 V  L  T  L   S  F  I    A  L  D    R  W  Y  A 147

441 CATCTGCCAC CCACTATTGT TCAAGAGCAC AGCCCGGCGG 480
147  I  C  H    P  L  L    F  K  S  T   A  R  R  160

481 GCCCGTGGCT CCATCCTGGG CATCTGGGCT GTGTCGCTGG 520
161  A  R  G    S  I  L  G   I  W  A    V  S  L  174

521 CCATCATGGT GCCCCAGGCT GCAGTCATGG AATGCAGCAG 560
174  A  I  M  V   P  Q  A   A  V  M    E  C  S  S 187

561 TGTGCTGCCT GAGCTAGCCA ACCGCACACG GCTCTTCTCA 600
187   V  L  P   E  L  A    N  R  T  R   L  F  S  200

601 GTCTGTGATG AACGCTGGGC AGATGACCTC TATCCCAAGA 640
201  V  C  D   E  R  W  A   D  D  L    Y  P  K   214

641 TCTACCACAG TTGCTTCTTT ATTGTCACCT ACCTGGCCCC 680
214  I  Y  H  S   C  F  F    I  V  T    Y  L  A  P 227
```

FIG. 2A

```
681  ACTGGGCCTC ATGGCCATGG CCTATTTCCA GATATTCCGC 720
227    L  G  L    M  A  M    A  Y  F  Q    I  F  R  240

721  AAGCTCTGGG GCCGCCAGAT CCCCGGCACC ACCTCAGCAC 760
241    K  L  W    G  R  Q  I    P  G  T    T  S  A  254

761  TGGTGCGGAA CTGGAAGCGC CCCTCAGACC AGCTGGGGGA 800
254  L  V  R  N    W  K  R    P  S  D  Q    L  G  D 267

801  CCTGGAGCAG GGCCTGAGTG GAGAGCCCCA GCCCCGGGGC 840
267    L  E  Q    G  L  S    G  E  P  Q    P  R  G  280

841  CGCGCCTTCC TGGCTGAAGT GAAGCAGATG CGTGCACGGA 880
281    R  A  F    L  A  E  V    K  Q  M    R  A  R  294

881  GGAAGACAGC CAAGATGCTG ATGGTGGTGC TGCTGGTCTT 920
294  R  K  T  A    K  M  L    M  V  V    L  L  V  F 307

921  CGCCCTCTGC TACCTCCCCA TCAGCGTCCT CAATGTCCTT 960
307    A  L  C    Y  L  P    I  S  V  L    N  V  L  320

961  AAGAGGGTGT TCGGGATGTT CCGCCAAGCC AGTGACCGCG 1000
321    K  R  V    F  G  M  F    R  Q  A    S  D  R  334

1001 AAGCTGTCTA CGCCTGCTTC ACCTTCTCCC ACTGGCTGGT 1040
334  E  A  V  Y    A  C  F    T  F  S    H  W  L  V 347

1041 GTACGCCAAC AGCGCTGCCA ACCCCATCAT CTACAACTTC 1080
347    Y  A  N    S  A  A    N  P  I  I    Y  N  F  360

1081 CTCAGTGGCC TTCCCTGGAG TCTGCTCTAA 1110
361    L  S  G    L  P  W  S    L  L  *    369
```

FIG. 2B

```
  1 ATGGAGCCCT CAGCCACCCC AGGGGCCCAG ATGGGGGTCC  40
  1   M  E  P   S  A  T  P   G  A  Q   M  G  V   14

41 CCCCTGGCAG CAGAGAGCCC TCCCCTGTGC CTCCAGACTA  80
 14  P  P  G  S   R  E  P   S  P  V   P  P  D  Y 27

81 TGAAGATGAG TTTCTCCGCT ATCTGTGGCG TGATTATCTG 120
 27   E  D  E   F  L  R   Y  L  W  R   D  Y  L   40

121 TACCCAAAAC AGTATGAGTG GGTCCTCATC GCAGCCTATG 160
 41  Y  P  K   Q  Y  E  W   V  L  I   A  A  Y    54

161 TGGCTGTGTT CGTCGTGGCC CTGGTGGGCA ACACGCTGGT 200
 54 V  A  V  F   V  V  A   L  V  G   N  T  L    67

201 CTGCCTGGCC GTGTGGCGGA ACCACCACAT GAGGACAGTC 240
 67   C  L  A   V  W  R   N  H  H   M  R  T  V   80

241 ACCAACTACT TCATTGTCAA CCTGTCCCTG GCTGACGTTC 280
 81  T  N  Y   F  I  V  N   L  S  L   A  D  V    94

281 TGGTGACTGC TATCTGCCTG CCGGCCAGCC TGCTGGTGGA 320
 94 L  V  T  A   I  C  L   P  A  S   L  L  V  D 107

321 CATCACTGAG TCCTGGCTGT TCGGCCATGC CCTCTGCAAG 360
107   I  T  E   S  W  L   F  G  H  A   L  C  K  120

361 GTCATCCCCT ATCTACAGGC TGTGTCCGTG TCAGTGGCAG 400
121  V  I  P   Y  L  Q  A   V  S  V   S  V  A   134

401 TGCTAACTCT CAGCTTCATC GCCCTGGACC GCTGGTATGC 440
134 V  L  T  L   S  F  I   A  L  D   R  W  Y  A 147

441 CATCTGCCAC CCACTATTGT TCAAGAGCAC AGCCCGGCGG 480
147   I  C  H   P  L  L   F  K  S  T   A  R  R  160

481 GCCCGTGGCT CCATCCTGGG CATCTGGGCT GTGTCGCTGG 520
161  A  R  G   S  I  L  G   I  W  A   V  S  L   174

521 CCATCATGGT GCCCCAGGCT GCAGTCATGG AATGCAGCAG 560
174 A  I  M  V   P  Q  A   A  V  M   E  C  S  S 187

561 TGTGCTGCCT GAGCTAGCCA ACCGCACACG GCTCTTCTCA 600
187   V  L  P   E  L  A   N  R  T  R   L  F  S  200

601 GTCTGTGATG AACGCTGGGC AGATGACCTC TATCCCAAGA 640
201  V  C  D   E  R  W  A   D  D  L   Y  P  K   214

641 TCTACCACAG TTGCTTCTTT ATTGTCACCT ACCTGGCCCC 680
214 I  Y  H  S   C  F  F   I  V  T   Y  L  A  P 227
```

FIG. 3A

```
 681 ACTGGGCCTC ATGGCCATGG CCTATTTCCA GATATTCCGC  720
 227   L  G  L   M  A  M   A  Y  F    Q  I  F  R  240

721 AAGCTCTGGG GCCGCCAGAT CCCCGGCACC ACCTCAGCAC  760
 241   K  L  W   G  R  Q  I   P  G  T   T  S  A   254

761 TGGTGCGGAA CTGGAAGCGC CCCTCAGACC AGCTGGGGGA  800
 254 L  V  R  N   W  K  R    P  S  D    Q  L  G  D 267

801 CCTGGAGCAG GGCCTGAGTG GAGAGCCCCA GCCCCGGGGC  840
 267   L  E  Q   G  L  S    G  E  P  Q   P  R  G  280

841 CGCGCCTTCC TGGCTGAAGT GAAGCAGATG CGTGCACGGA  880
 281   R  A  F   L  A  E  V   K  Q  M   R  A  R   294

881 GGAAGACAGC CAAGATGCTG ATGGTGGTGC TGCTGGTCTT  920
 294 R  K  T  A   K  M  L   M  V  V    L  L  V  F 307

921 CGCCCTCTGC TACCTGCCCA TCAGCGTCCT CAATGTCCTT  960
 307   A  L  C   Y  L  P   I  S  V  L   N  V  L   320

961 AAGAGGGTGT TCGGGATGTT CCGCCAAGCC AGTGACCGCG 1000
 321   K  R  V   F  G  M  F   R  Q  A   S  D  R   334

1001 AAGCTGTCTA CGCCTGCTTC ACCTTCTCCC ACTGGCTGGT 1040
 334 E  A  V  Y   A  C  F    T  F  S   H  W  L  V 347

1041 GTACGCCAAC AGCGCTGCCA ACCCCATCAT CTACAACTTC 1080
 347   Y  A  N   S  A  A   N  P  I  I   Y  N  F   360

1081 CTCAGTGGAT GTAAAGAGAA GAGTCTAGTT CTGTCCTGAC 1120
 361   L  S  G   C  K  E  K   S  L  V   L  S  *   374

1121 CATCGTGCCC CGG 1133
 374  P  S  C  P  G  378
```

FIG. 3B

1   MEPSATPGAQMGVPPGSREPSPVPPDYEDEFLRYLWRDYLYPKQYEWVLIA   51
                                                TM1
52  AYVAVFVVALVGNTLVCLAVWRNHHMRTVTNYFIVNLSLADVLVTAICLPA  102
                                    TM2
103 SLLVDITESWLFGHALCKVIPYLQAVSVSVAVLTLSFIALDRWYAICHPLL  153
            TM3
154 FKSTARRARGSILGIWAVSLAIMVPQAAVMECSSVLPELANRTRLFSVCDE  204
                TM4
205 RWADDLYPKIYHSCFFIVTYLAPLGLMAMAYFQIFRKLWGRQIPGTTSALV  255
           TM5
256 RNWKRPSDQLGDLEQGLSGEPQPRGRAFLAEVKQMRARRKTAKMLMVLLV   306
                                              TM6
307 FALCYLPISVLNVLKRVFGMFRQASDREAVYACFTFSHWLVYANSAANPII  357
        TM7
358 YNFLSGKFREQFKAAFSCCLPGLGPCGSLKAPSPRSSASIIKSLSL*     402

FIG. 4

1    MEPSATPGAQMGVPPGSREPSPVPPDYEDEFLRYLWRDYLYPKQYEWVLIA    51

52   AYVAVFVVALVGNTLVCLAVWRNHHMRTVTNYFIVNLSLADVLVTAICLPA   102
     TM1                                    TM2

103  SLLVDITESWLFGHALCKVIPYLQAVSVSVAVLTLSFIALDRWYAICHPLL   153
     TM3

154  FKSTARRRARGSILGIWAVSLAIMVPQAAVMECSSVLPELANRTRLFSVCDE  204
              TM4

205  RWADDLYPKIYHSCFFIVTYLAPLGLMAMAYFQIFRKLWGRQIPGTTSALV   255
                         TM5

256  RNWKRPSDQLGDLEQGLSGEPQPRGRAFLAEVKQMRARRKTAKMLMVVLLV   306
                                            TM6

307  FALCYLPISVLNVLKRVFGMFRQASDREAVYACFTFSHWLVYANSAANPII   357
                                 TM7

358  YNFLSGLPWSLL*  369

FIG. 5

| | |
|---|---|
| 1 | MEPSATPGAQMGVPPGSREPSPVPPDYEDEFLRYLWRDYLYPKQYEWVLIA | 51 |

TM1

| | |
|---|---|
| 52 | AYVAVFVVALVGNTLVCLAVWRNHHMRTVTNYFIVNLSLADVLVTAICLPA | 102 |

TM2

TM3

| | |
|---|---|
| 103 | SLLVDITESWLFGHALCKVIPYLQAVSVSVAVLTLSFIALDRWYAICHPLL | 153 |

TM4

| | |
|---|---|
| 154 | FKSTARRARGSILGIWAVSLAIMVPQAAVMECSSVLPELANRTRLFSVCDE | 204 |

TM5

| | |
|---|---|
| 205 | RWADDLYPKIYHSCFFIVTYLAPLGLMAMAYFQIFRKLWGRQIPGTTSALV | 255 |

| | |
|---|---|
| 256 | RNWKRPSDQLGDLEQGLSGEPQPRGRAFLAEVKQMRARRKTAKMLMVVLLV | 306 |

TM6

| | |
|---|---|
| 307 | FALCYLPISVLNVLKRVFGMFRQASDREAVYACFTFSHWLVYANSAANPII | 357 |

TM7

| | |
|---|---|
| 358 | YNFLSGCKEKSLVLS*372 | |

FIG. 6

```
  8 GAQMGVPPGSREPSPVPPDYEDEFLRYLWRDYLYPKQYEWVLIAAYVAVF  57
    ..   ..  .. ...  .  .  | .   | .|  . | ||.||.
    ..  .  .. ....    |  .  |. | . .|  ||.||.
  2 NSTLFSQVENHSVHSNFSEKNAQLLAFENDDCHLPLAMIFTLALAYGAVI  51

58 VVALVGNTLVCLAVWRNHHMRTVTNYFIVNLSLADVLVTAICLPASLLVD 107
    ....  ||  . . ...  ||.|||.|||||.|.||.  .|||  ..
    ....  ||  ... ......||.|||..|||||..|.||..|||  ...
 52 ILGVSGNLALIIIILKQKEMRNVTNILIVNLSFSDLLVAIMCLPFTFVYT 101

108 IYESWLFGHALCKVIPYLQAVSVSVAVLTLSFIALDRWYAICHPLLFKST 157
    .. |:||.|. . |.. .||. . . | .||..|  |.|  ..
    .. |.|.|.   |.. ||. ... .||..| ..| ....
102 LMDHWVFGEAMCKLNPFVQCVSITVSIFSLVLIAVERHQLIINPRGWRPN 151

158 ARRARGSILGIW....AVSLAIMVPQAAVMECSSVLPELANRTRLFSVCD 203
    .|.|  .|  .||    |||.|...|..|.   ..|  |..  ||
    .|.|  .| .||    |||.|...|. |.  .. |   ..  ||
152 NRHAYVGIAVIWVQAVASSLPFLIYQVMTDEPFQNVTLDAYKDKY..VCF 199

204 ERWADDLYPKIYHSCFFIVTYLAPLGLMAMAYFQIFRKLWGRQIPGTTSA 253
    .  ..  |     |  ....  |..||   .. ||.|.. .
    .....  |  ..  . ....  ..||...  ..||.|..
200 DQFPSDSHRLSYTTLLLVLQYFGPLCFIFICYFKIYIRL........... 238

254 LVRNWKRPSDQLGDLEQGLSGEPQPRGRAFLAEVKQMRARRKTAKMLMVV 303
       ||.. ... .        .               ...||.|..
       ||...  ....        .                ....||.|..
239 .....KRRNNMMDKMRDNKYRSSET...............KRINIMLLSI 268

304 LLVFALCYLPISVLNVLKRVFGMFRQASDREAVYACFTFSHWLVYANSAA 353
    ..||.|.||....||.||....    ....|.|.  .  ..|..|.
    ...||.|.||....|.||....    ||..|.|      ..|..|.
269 VVAFAVCWLPLTIFNT...VFDWNHQIIATCNHNLLFLLCHLTAMISTCV 315

354 NPIIYNFLSGKFREQFKAAFSCC..LPGLGPCGSLKAPSPRSSASHKSLS 401
    |||.|||.|.|.||. ..|.|  ...  .|.|  ...  .|..|
    |||.|.||..|.||... ||.|   ...   .|.|   ...|..||.
316 NPIFYGFLNKNFQRDLQFFFNFCDFRSRDDDYETIAMSTMHTDVSKTSLK 365
```

FIG. 7

HUMAN NEUROPEPTIDE RECEPTOR

This invention relates to newly identified polynucleotides, polypeptides encoded by such polynucleotides, the use of such polynucleotides and polypeptides, as well as the production of such polynucleotides and polypeptides. The polypeptides of the present invention are human 7-transmembrane G-protein coupled receptors. More particularly, the polypeptides of the present invention are neuropeptide receptor polypeptides, sometimes hereinafter referred to as neuropeptide receptor polypeptides. The invention also relates to inhibiting the action of such polypeptides.

Obesity is the commonest nutritional disorder in Western societies. More than three in ten adult Americans weigh at least 20% in excess of their ideal body weight (Burroa, M., The New York Times, Jul. 17, 1994). Increased body weight is an important public health problem because it is associated with Type II diabetes, hypertension, hyperlipidemia and certain cancers (Grundy, S. M., and Barnett, J. P., Disease-a-Month, 36:645–696 (1990)).

Five single-gene mutations in the mouse obesity gene (ob) which result in an obese phenotype have been described (Friedman, J. M. & Leibel, R. L., Cell, 66:217–220 (1990)). The cloning and sequencing of the mouse ob gene and its human homologue have been reported (Zhang, Y., et al., Nature, 372:425–431 (1994)). The ob gene encodes a 4.5-kb adipose tissue mRNA with a highly conserved 167-amino-acid open reading frame. The predicted amino-acid sequence is 84% identical between human and mouse and has features of a secreted protein. The ob gene product may function as part of a signalling pathway from adipose tissue that acts to regulate the size of the body fat depot (id. 425).

Of the brain regions implicated in the regulation of feeding behavior, the ventromedial nucleus of the hypothalamus (VMH) is considered to be the most important satiety center in the central nervous system (CNS). The energy balance in mammals is therefore postulated to be controlled by a feedback loop in which the amount of stored energy is sensed by the hypothalamus, which adjusts food intake and energy expenditure to maintain a constant body weight (Ombeck, J. R., Yale J. Biol. Med., 20:545–552 (1948) and Kennedy, G. C., Proc. R. Soc. 148:578–592 (1953)). In the lipostasis theory, the size of the body fat depot is regulated by the CNS, with a product of body fat metabolism affecting energy balance by interacting with the hypothalamus (Kennedy, G. C., Proc. R. Soc. 148:578–592 (1953)).

The inability to identify the putative signal from fat has hindered the validation of the lipostasis theory. The possibility that at least one component of the signalling system circulates in the bloodstream was first suggested by Hervey (Dietrich, W., et al., Genetics, 131:423–447 (1992)), who showed that the transfer of blood from an animal with a VMH lesion across a vascular graft to an untreated animal (a parabiosis experiment) resulted in a reduction of food intake in the intact animal. It is now significant that there is evidence that the ob gene product is secreted, suggesting that ob may encode this circulating factor.

The ob signal may act directly or indirectly on the CNS to inhibit food intake and/or regulate energy expenditure as part of a homeostatic mechanism to maintain constancy of the adipose mass (Zhang, Y., et al., Nature, 372:425–431, 431 (1994)). The ob gene apparently encodes a protein secreted by fat, and mutations apparently prevent translation or expression of the gene (Rink, T., Nature, 372:406–407 (1994)).

Parabiosis experiments suggest that the ob receptor is encoded by the mouse db (diabetes) gene (Coleman, D. L., Diabetologia, 14:141–148 (1978)). Mice having a mutation in the db gene are also obese, with the defect possibly being a receptor defect. (Id. at 406).

Neuropeptide Y is similar to the ob gene product in that it mediates the feeding response. Neuropeptide Y acts on at least four types of neuropeptide Y receptors called $Y_1$, $Y_2$, $Y_3$ and an atypical $Y_1$ receptor, which mediates the feeding response stimulated by neuropeptide Y.

Neuropeptide Y has a wide range of biological functions. Neuropeptide Y is found to be widely distributed in the central nervous system (CNS) and the peripheral nervous system (PNS). In the PNS, neuropeptide Y is found in the noradrenergic sympathetic innervation of blood vessels and other smooth muscle tissues and in neurons within the enteric nervous system. Neuropeptide Y immunoreactive fibers also occur in the non-vascular smooth muscle, surrounding exocrine glands and surface epithelia. Neuropeptide Y also occurs in subpopulations of neurons and is generally co-localized with other neurotransmitters, particular noradrenaline.

In the CNS, neuropeptide Y is contained in GABAergic interneurons in higher centers and in predominantly catecholaminergic cells that project further caudally. For example, neuropeptide Y is contained in interneurons in the cortex, hippocampus, amygdala, basal forebrain and striatum, whereas in the brain stem, neuropeptide Y is contained in noradrenergic neurons of the $A_1$ and $A_2$ groups in the medulla, and the locus coeruleus (LC). In the hypothalamus, neuropeptide Y is found predominantly in the arcuate nucleus and lateral hypothalamus.

Within the peripheral nervous system, neuropeptide Y is present in postganglionic sympathetic nerves, and is co-localized as stated above with other neurotransmitters, including catecholamines. When used pharmacologically, neuropeptide Y has been shown to have a potent vasoconstrictor activity as well as dramatically potentiating the vasoconstriction caused by many other pressor agents. Particularly high concentrations of neuropeptide Y are found in the sympathetic nerves supplying the coronary, cerebral and renal vasculature and when infused into these vascular beds, neuropeptide Y causes prolonged vasoconstriction that is not reversed by adrenergic blocking agents. These observations have lead to the proposal that neuropeptide Y is the candidate transmitter for pathological vasospasm, a major cause of morbidity and mortality when involving the coronary and cerebral vessels.

Neuropeptide Y also appears to be involved in interaction with the renin angiotensin system. Neuropeptide Y containing sympathetic nerve terminals are found on the juxtaglomerular apparatus of the renal cortex and neuropeptide Y influences renin release. These data, together with the demonstration of all durations in neuropeptide Y concentrations in hypertensive animal models and the pressor response to infusion of the peptide, have resulted in implications of this peptide in hypertension.

Within the central nervous system neuropeptide Y is located predominantly within interneurons where it appears to have a regulatory role. It therefore has widespread and diverse effects including effects on memory and a possible role in Alzheimer's disease. Neuropeptide Y is the most potent known substance to cause an increase in feeding and may play a role in the genetic basis of Type II Diabetes Mellitus. Neuropeptide Y may also play a role as a regulatory agent and pituitary function as well as potential neuromodulatory function in stress responses and in reproductive function.

In accordance with one aspect of the present invention, there are provided novel mature receptor polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the receptor polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention which are useful in the prevention and/or treatment of obesity, hyperlipidemia, certain cancers, to stimulate neuronal growth, to regulate neurotransmission, to enhance activity levels and utilization of ingested foods.

In accordance with another aspect of the present invention there is provided a method of administering the receptor polypeptides of the present invention via gene therapy to treat conditions related to underexpression of the polypeptides or underexpression of a ligand to the receptor polypeptide.

In accordance with still another embodiment of the present invention there are provided processes of administering compounds to a host which bind to and inhibit activation of the receptor polypeptides of the present invention which are useful in the prevention and/or treatment of Alzheimer's disease, Type II Diabetes Mellitus, epilepsy, stress, anxiety, hypertension, cardiovascular disease, psychotic conditions and obesity caused by neuropeptide Y.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 1A and 1B shows the cDNA sequence (SEQ ID NO:1) and the corresponding deduced amino acid sequence (SEQ ID NO:2) of the fneuropeptide receptor polypeptide of the present invention. The standard one-letter abbreviation for amino acids is used. Sequencing was performed using a 373 Automated DNA sequencer (Applied Biosystems, Inc.).

FIGS. 2A and 2B shows the cDNA sequence and the corresponding deduced amino acid sequence of the neuropeptide receptor splice variant 1 polypeptide of the present invention. The standard one-letter abbreviation for amino acids is used.

FIGS. 3A and 3B shows the cDNA sequence and the corresponding deduced amino acid sequence of the neuropeptide receptor splice variant 2 polypeptide of the present invention. The standard one-letter abbreviation for amino acids is used.

FIG. 4 illustrates the amino acid sequence and seven transmembrane regions of the neuropeptide receptor. The transmembrane regions are underlined and denoted with a TM.

FIG. 5 illustrates the amino acid sequence and seven transmembrane regions of the neuropeptide receptor splice variant 1. The transmembrane regions are underlined and denoted with a TM.

FIG. 6 illustrates the amino acid sequence and seven transmembrane regions of the neuropeptide receptor splice variant 2. The transmembrane regions are underlined and denoted with a TM.

FIG. 7 shows the amino acid homology between the human neuropeptide receptor polypeptide of the present invention (and the human neuropeptide $Y_1$ receptor).

The receptor polypeptides of the present invention are receptors for ligands, both known and unknown, which modulate the activity of cells in both the central nervous system and peripheral tissues regulated by the central nervous system. Examples of such ligands are neuropeptide Y, substance P, the human ob gene product and neurokinin B. Accordingly, modulation of the activity of receptor polypeptides of the present invention will have a broad range of therapeutic and diagnostic applications, particularly with respect to the treatment of obesity.

The present inventors have isolated a full-length cDNA clone encoding a human neuropeptide receptor polypeptide. The present full-length cDNA has been mapped to a location on human chromosome 1 position p31–34 which corresponds to a location on the mouse chromosome 4 where the db gene is found. The mouse db gene is thought to encode the receptor for the obesity gene product.

In accordance with an aspect of the present invention, there are provided isolated nucleic acids (polynucleotides) which encode for the mature polypeptide having the deduced amino acid sequence of FIGS. 2A and 2B (SEQ ID NO:2) or for the mature polypeptide encoded by the cDNA of the clone(s) deposited as ATCC Deposit No. 97128 on Apr. 28, 1995.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

The polynucleotide of this invention was discovered in a DNA library derived from human adult hypothalamus. It is structurally related to the G protein-coupled receptor family. The neuropeptide receptor polypeptide contains an open reading frame encoding a protein of 402 amino acid residues. The neuropeptide receptor protein exhibits the highest degree of homology to human neuropeptide $Y_1$ receptor protein with 52% similarity and 26% identity over the entire amino acid sequence.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequences which encode the mature polypeptide may be identical to the coding sequence shown in FIGS. 1A and 1B (SEQ ID NO:1) or that of the deposited clone(s) or may be a different coding sequence which coding sequence, as a result of the redundancy or degeneracy of the genetic code, encodes the same mature polypeptide as the DNA of FIGS. 1A and 1B (SEQ ID NO:1) or the deposited cDNA(s).

The polynucleotides which encode for the mature polypeptide of FIGS. 2A and 2B (SEQ ID NO:2) or for the mature polypeptide encoded by the deposited cDNA(s) may include: only the coding sequence for the mature polypeptide; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequence of FIGS. 2A and 2B (SEQ ID NO:2) or the polypeptide encoded by the cDNA of the deposited clone(s). The variants of the polynucleotide may be naturally occurring allelic variants of the polynucleotides or non-naturally occurring variants of the polynucleotides.

Thus, the present invention includes polynucleotides encoding the same mature polypeptide as shown in FIGS. 2A and 2B (SEQ ID NO:2) or the same mature polypeptide encoded by the cDNA of the deposited clone(s) as well as variants of such polynucleotide which variants encode for a fragment derivative or analog of the polypeptide of FIGS. 2A and 2B (SEQ ID NO:2) or the polypeptide encoded by the cDNA of the deposited clone(s). Such nucleotide variants include deletion variants, substitution variants and addition or insertion variants. Specific examples of such variants include the polynucleotide sequences as set forth in SEQ ID NOS:3 and 5 which encode for splice variant 1 and 2, respectively, of the polypeptide of the present invention.

As hereinabove indicated, the polynucleotides may have a coding sequence which is a naturally occurring allelic variant of the coding sequence shown in FIGS. 1A and 1B (SEQ ID NO:1) or of the coding sequence of the deposited clone(s). As known in the art, an allelic variant is an alternate form of polynucleotide sequences which may have a substitution, deletion or addition of one or more nucleotides, which does not substantially alter the function of the encoded polypeptides.

The polynucleotides may also encode for a soluble form, of the neuropeptide receptor polypeptide which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A, and 1B, 2A, 2B, and 3A and 3B (SEQ ID NO:1, 3 and 5) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, 3 and 5, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2, 4 and 6 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIGS. 2A and 2B (SEQ ID NO:2) or which has the amino acid sequence encoded by the deposited cDNA(s), as well as fragments, analogs and derivatives of such polypeptide.

The terms "fragment," "derivative" and "analog" when referring to the polypeptide of FIGS. 2A and 2B (SEQ ID NO:2) or that encoded by the deposited cDNA(s), means polypeptides which either retain substantially the same biological function or activity as such polypeptides, i.e., function as a soluble neuropeptide receptor by retaining the ability to bind the ligands of the receptors even though the polypeptides do not function as membrane bound neuropeptide receptors. An analog includes a proprotein which can be activated by cleavage of the proprotein portion to produce an active mature polypeptide. Specific examples are splice variant 1 and 2 of FIGS. 2A, 2B, 3A, and 3B (SEQ ID NO:4 and 6), respectively.

The polypeptides of the present invention may be recombinant polypeptides, natural polypeptides or synthetic polypeptides, preferably recombinant polypeptides.

A fragment, derivative or analog of the polypeptide of FIGS. 2A and 2B (SEE ID NO:2) or that encoded by the deposited cDNA(s) may be (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the mature polypeptide is fused with another compound, such as a compound to increase the half-life of the polypeptide (for example, polyethylene glycol), (iv) one in which the additional amino acids are fused to the mature polypeptide, such as sequence which is employed for purification of the mature polypeptide sequence or (iv) splice variants of the mature polypeptide which may have one or more amino acids deleted from the mature polypeptide yet still retain activity corresponding to the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2, 4 and 6 (in particular the mature polypeptide) as well as polypeptides which have at least 70% similarity (preferably at least 70% identity) to the polypeptide of SEQ ID NO:2, 4 and 6 and more preferably at least 90% similarity (more preferably at least 90? identity) to the polypeptide of SEQ ID NO:2, 4 and 6 and still more preferably at least 95% similarity (still more preferably at least 95% identity) to the polypeptide of SEQ ID NO:2, 4 and 6 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the human neuropeptide receptor genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli.* lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli*, Streptomyces, *Salmonella typhimurium*; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); pTRC99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, PMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The neuropeptide receptor polypeptide of the present invention can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The neuropeptide receptor polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The human neuropeptide receptor polypeptides of the present invention may be employed in a process for screening compounds which bind to and activate the receptor polypeptide and for compounds which bind to and inhibit activation of the receptor polypeptides of the present invention.

In general, the neuropeptide receptor is isolated, immobilized or cell bound form is contacted with a plurality of compounds and those compounds are selected which bind to and interact with the receptor. The binding or interaction can be measured directly by using radioactively labeled compounds of interest or by the second messenger effect resulting from the interaction or binding of the candidate compound. Alternatively, the candidate compounds can be subjected to competition screening assays, in which a known ligand, preferably labeled with an analytically detectable reagent, most preferably radioactivity, is introduced with the compound to be tested and the compound's capacity to inhibit or enhance the binding of the labeled ligand is measured. Compounds are screened for their increased afffinity and selectivity to the receptor polypeptide of the present invention.

One such screening procedure involves the use of melanophores which are transfected to express the neuropeptide receptor of the present invention. Such a screening technique is described in PCT WO 92/01810 published Feb. 6, 1992.

For example, to screen for compounds which inhibit activation of the receptor polypeptide of the present invention, the compound and a ligand known to bind to the receptor are both contacted with the melanophore cells. Inhibition of the signal generated by the ligand indicates that the compound inhibits activation of the receptor.

The screen may be employed for determining a compound which binds to and activates the receptor polypeptide of the present invention by contacting such cells with compounds to be screened and determining whether such compound generates a signal, i.e., activates the receptor.

Other examples include the use of cells which express a neuropeptide receptor of the present invention (for example, transfected CHO cells) in a system which measures extracellular pH changes caused by receptor activation, for example, as described in Science, volume 246, pages 181–296 (October 1989). For example, compounds may be contacted with a cell which expresses an neuropeptide receptor polypeptide of the present invention and a second messenger response, e.g. signal transduction or pH changes, may be measured to determine whether the potential compound is effective as an activator or inhibitor.

Another example involves introducing RNA encoding a neuropeptide receptor of the present invention into Xenopus oocytes to transiently express the receptor. The oocytes may then be contacted with the receptor ligand and a compound to be screened, followed by detection of inhibition of or an increase in intracellular calcium.

Another example involves expressing a neuropeptide receptor polypeptide of the present invention on the surface of a cell wherein the receptor is linked to a phospholipase C or D. As representative examples of such cells there may be mentioned endothelial cells, smooth muscle cells, embryonic kidney cells, etc. The screening may be accomplished as hereinabove described by detecting activation of the receptor or inhibition of activation of the receptor from the phospholipase second signal.

Another method involves determining inhibition of binding of labeled ligand to cells which have a neuropeptide receptor on the surface thereof. Such a method involves transfecting a eukaryotic cell with DNA encoding an neuropeptide receptor polypeptide of the present invention such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Another screening technique involves expressing a neuropeptide receptor polypeptide on the surface of a cell wherein the receptor is linked to a second messenger to increase cytosolic calcium levels in transfected CHO cells. An example of such a method comprises transfecting CHO cells with a nucleic acid sequence encoding a receptor of the present invention such that the receptor is expressed on the surface thereof. The transfected cell is then incubated in a reaction mixture with labeled calcium in the presence of a compound to be screened. The ability of the compound to increase calcium up-take or inhibit calcium up-take can then be determined by measuring the amount of labeled calcium transported into the cells by taking advantage of the label, e.g., radioactivity.

Compounds may also be identified by the above methods which bind to specific subregions within the CNS that are important for specific behaviors through indirect interactions with a neuropeptide receptor polypeptide of the present invention.

To measure intracellular cyclic AMP levels, cyclic AMP is assayed in whole cells treated for 15 minutes at 37° C. with 100 micromolar isobutylmethylxanthine (IBMX; Sigma). Transfected cells ($1\times10^6$/0.5 ml reaction) are incubated with 10 micromolar forskolin and various concentrations of known or unknown ligands to the receptor. Reactions are terminated with the addition of HCl to 0.1M, incubation at room temperature for 15 minutes, neutralization and sample dilution in 50 mM sodium acetate, pH 6.2. Cyclic AMP is quantified by using a radioimmunoassay (Dupont/NEN).

To measure levels of intracellular calcium, transfected cells are suspended in loading medium (modified RPMI 1640 medium/10 mM Hepes/1% newborn calf serum) and incubated in a spinner flask at 37° C. for 2.5 hour at $1\times10^6$ cells per ml. Cells are then treated with 1 micromolar Fura-2 acetoxymethyl ester (fura-2 AM; Molecular Probes) for 30 minutes at 37° C., washed twice with loading medium, and resuspended at $5\times10^6$ cells/ml. Immediately before fluorescence spectroscopy, cells are recovered by centrifugation at 1000 rpm and resuspended at $1\times10$ cells/ml in a modified Krebs buffer (135 mM NaCl/4.7 mM KCl/1.2 mM $MgSO_4$/ 1.2 mM $KH_2PO_4$/5 mM $NaHCO_3$/1 mM $CaCl_2$/2.8 mM glucose/10 mM hepes, pH 7.4) containing sulfinpyrazone. Bombesin is purchased from Sigma and Auspep. Fluorescence recordings are made on a Hitachi fluorescence spectrometer (F4010) at 340 nm (excitation) and 505 nm (emission) over 10 minutes with slit widths of 5 nm and response time of 2 seconds. Intracellular calcium is quantified by using equations described by Grynkiewicz, et al., J. Bio. Chem. 260:3440–3450, 1985.

The invention also provides a method of treating and/or preventing obesity by administering to a host a compound which binds to and activates the receptor polypeptides of the present invention. Such a compound is other than the ob gene product disclosed in Zhang, et al., Nature, 372:425–431 (1994). The receptor polypeptide of the present invention maps to a human chromosome which corresponds to the position of the mouse chromosome which encodes for the receptor of the ob gene product. The human ob gene encodes a "satiety" factor which binds to and activates the receptor polypeptide of the present invention. Accordingly, a compound which activates the receptor of the present invention will decrease appetite and prevent obesity.

The compounds described above may also be employed to enhance activity level, modify eating behavior, enhance utilization of ingested foods and regulate deposition of fat stores. Conditions related to obesity may also be treated by the compounds which bind to and activate the receptor polypeptides of the present invention including hyperlidimeia, type II diabetes and certain cancers.

These compounds may also be employed to treat and/or prevent other conditions related to an underexpression of the receptor polypeptide of the present invention or ligands which bind thereto, for example, to stimulate neuronal growth.

Specific examples of compounds which inhibit activation of the receptor polypeptides of the present invention include an antibody, or in some cases an oligonucleotide, which binds to the receptor but does not elicit a second messenger response such that the activity of the receptor is prevented.

Another example is proteins which are closely related to the ligands of the receptor, i.e. a fragment of the ligand, which have lost biological function and when binding to the receptor, elicit no response.

Another example includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix see Lee et al., Nucl. Acids Res., 6:3073 (1979); Cooney et al, Science, 241:456 (1988); and Dervan et al., Science, 251: 1360 (1991)), thereby preventing transcription and the production of a neuropeptide receptor polypeptide of the present invention. The antisense RNA oligonucleotide hybridizes to the mRNA in vivo and blocks translation of the mRNA molecule into the receptor (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the receptors.

Another example is a small molecule which binds to a neuropeptide receptor polypeptide of the present invention, making it inaccessible to ligands such that normal biological activity is prevented. Examples of small molecules include but are not limited to small peptides or peptide-like molecules and neuropeptide Y fragments and/or derivatives.

Soluble forms of a neuropeptide receptor polypeptide of the present invention, e.g., a fragment of the receptor, which binds to the ligand and prevents the ligand from interacting with membrane bound receptors may also inhibit activation of the receptor polypeptides of the present invention.

This invention additionally provides a method of utilizing such compounds which inhibit activation for treating abnormal conditions related to an excess of activity of a neuropeptide receptor polypeptide of the present invention for treating obesity since the neuropeptide receptor polypeptides of the present invention may bind neuropeptide Y which is the most potent known substance to cause an increase in feeding behavior and type II Diabetes Mellitus since neuropeptide Y may play a role in the genetic basis of this disease.

The compounds which inhibit activation of the receptor polypeptides of the present invention may be employed to treat and/or prevent hypertension since neuropeptide Y stimulates renin release and neuropeptide Y is known to have potent vasoconstrictor activity when involving the coronary and cerebral vessels.

The compounds may also be employed to treat Alzheimer's disease since neuropeptide Y receptors are prevalent in the central nervous system and are localized predominantly within interneurons where they appear to have regulatory roles in memory and Alzheimers disease.

The compounds may also be employed to suppress excitatory transmission by neuropeptide Y in the hippocampus and therefore may be employed to treat epileptic seizure, stress and anxiety.

The prevalence of neuropeptide Y receptors in the central nervous system indicates that the compounds which inhibit the neuropeptide receptor polypeptides of the present invention may be used as an antipsychotic drug by regulating neurotransmission.

The compounds which inhibit the receptor polypeptides of the present invention may also be employed to treat pathological vasospasm involving coronary and cerebral vessels.

This invention also provides a method for determining whether a ligand not known to be capable of binding to a neuropeptide receptor of the present invention can bind thereto which comprises contacting the ligand to be identified with a cell comprising the coding sequence of a neuropeptide receptor and expressing same on its surface under conditions sufficient for binding of ligands previously identified as binding to such a receptor. In other embodiments cell membrane fractions comprising the receptor or isolated receptors free or immobilized on solid supports may be used to measure binding of the ligand to be tested. When recombinant cells are used for purposes of expression of the receptor it is preferred to use cells with little or no endogenous receptor activity so that binding, if any, is due to the presence of the expressed receptor of interest. Preferred cells include human embryonic kidney cells, monkey kidney (HEK-293 cells), fibroblast (COS) cells, Chinese hamster ovary (CHO) cells, Drosophila or murine L-cells. It is also preferred to employ as a host cell, one in which a receptor responsive second messenger system exists. Well known-second messenger systems include increases or decreases in phosphoinositide hydrolysis, adenylate cyclase, guanylate cyclase, or ion channel activity in response to ligand binding to extracellular receptor domains. In a further embodiment a specifically designed indicator of receptor binding can be constructed. For example, a fusion protein can be made by fusing the receptor of this invention with a protein domain which is sensitive to receptor ligand binding. Such a domain referred to here as an indicator domain is capable, itself, or in association with accessory molecules, of generating an analytically detectable signal which is indicative or receptor ligand binding.

This invention also provides a method of detecting expression of a neuropeptide receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a neuropeptide receptor polypeptide of the present invention, by low stringency cross hybridization, or by identifying receptors that interact with related natural or synthetic ligands and or elicit similar behaviors after genetic or pharmacological blockade of the neuropeptide receptor polypeptides of the present invention.

Fragments of the genes may be used as a hybridization probe for a cDNA library to isolate other genes which have a high sequence similarity to the genes of the present invention, or which have similar biological activity. Probes of this type preferably have 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The neuropeptide receptor polypeptides and compounds identified above which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter;

the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The soluble neuropeptide receptor polypeptides and compounds which bind to and activate or inhibit activation of a receptor of the present invention may also be employed in combination with a suitable pharmaceutical carrier. Such compositions comprise a therapeutically effective amount of the soluble neuropeptide receptor polypeptide or compounds, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the soluble neuropeptide receptor polypeptides or compounds of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., colorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the neuropeptide receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the neuropeptide receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any neuropeptide receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to neuropeptide receptor proteins. Unattached reporter antibody is then washed out. Peroxidase substrates are then added to the dish and the amount of color developed in a given time period is a measurement of the amount of neuropeptide receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases.

For a review of this technique, see Verma et al., Human Chromosomes: a Manual of Basic Techniques, Pergamon Press, New York (1988).

The above techniques were utilized to map the gene corresponding to the neuropeptide receptor of the present invention to chromosome 1 position 31–34.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980). "Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of the Neuropeptide Receptor

The DNA sequence encoding for neuropeptide receptor, ATCC #97128 is initially amplified using PCR oligonucleotide primers corresponding to the 5' and 3' end sequences of the processed neuropeptide receptor gene (minus the signal peptide sequence) and the vector sequences 3' to the gene. Additional nucleotides corresponding to neuropeptide receptor nucleotide sequence are added to the 5' and 3' sequences respectively. The 5' oligonucleotide primer has the sequence 5' CACTAAAGCTTAATGGAGCCCT-CAGCCACC 3' (SEQ ID NO:7) contains a Hind III restriction enzyme site followed by 18 nucleotides of neuropeptide receptor coding sequence starting from the presumed terminal amino acid of the processed protein codon. The 3' sequence 5' ACAAGTCCTTGTCCTTCTAGAGGGC 3' (SEQ ID NO:8) and contains an Xba1 site. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with Hind III and Xba1. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized neuropeptide receptor is purified from this solution by chromatography on a Nickel-Chelate column under conditions that allow for tight binding by proteins containing the 6-His tag (Hochuli, E. et al., J. Chromatography 411:177–184 (1984). The protein is eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

EXAMPLE 2

Expression of Recombinant Neuropeptide Receptor in COS Cells

The expression of plasmid, neuropeptide receptor HA is derived from a vector pcDNA3/Amp (Invitrogen) containing: 1) SV40 origin of replication, 2) ampicillin resistance gene, 3) E. coli replication origin, 4) CMV promoter followed by a polylinker region, a SV40 intron and polyadenylation site. A DNA fragment encoding the entire neuropeptide receptor precursor and a HA tag fused in frame to its 3' end is cloned into the polylinker region of the vector, therefore, the recombinant protein expression is directed under the CMV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37, 767). The infusion of HA tag to the target protein allows easy detection of the recombinant protein with an antibody that recognizes the HA epitope.

The plasmid construction strategy is described as follows:

The DNA sequence encoding for neuropeptide receptor, ATCC #97128, is constructed by PCR using two primers: the 5' primer 5' CCTAGGATGCCCCTCTGCTGCAGCGG 3' (SEQ ID NO:9) contains a BamHI site; the 3' sequence 5' ACAAGTCCTTGTCCTTCTAGAGGGC 3' (SEQ ID NO:10) contains complementary sequences to an XbaI site, translation stop codon, and the last 17 nucleotides of the neuropeptide receptor coding sequence (not including the stop codon). Therefore, the PCR product contains a BamHI site, coding sequence, a translation termination stop codon and an XbaI site. The PCR amplified DNA fragment and the vector, pcDNA3/Amp, are digested with BamHI and XbaI restriction enzymes and ligated. The ligation mixture is transformed into E. coli strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant neuropeptide receptor, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the neuropeptide receptor HA protein is detected by radio-labelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 150 SDS-PAGE gels.

EXAMPLE 3

Cloning and Expression of Neuropentide Receptor Using the Baculovirus Expression System The DNA sequence encoding the full length neuropeptide receptor protein, ATCC #97128, is amplified using PCR oligonucleotide primers corresponding to the 5' and 3' sequences of the gene:

The 5' primer has the sequence 5' CGGGATCCGCCATC ATGGAGCCCTCAGCCACC 3' (SEQ ID NO:11) and contains a BamHI restriction enzyme site (in bold) followed by 6 nucleotides resembling an efficient signal for the initiation of translation in eukaryotic cells (J. Mol. Biol. 1987, 196, 947–950, Kozak, M.). The initiation codon for translation "ATG" is underlined).

The 3' primer has the sequence 5' ACAAGTCCTTGTCCTTCTAGAGGGC 3' (SEQ ID NO:12) and contains the cleavage site for the restriction endonuclease XbaI and 5 nucleotides complementary to the 3' non-translated sequence of the neuropeptide receptor gene. The amplified sequences are isolated from a 1% agarose gel using a commercially available kit ("Geneclean," BIO 101 Inc., La Jolla, Calif.). The fragment is then digested with the endonucleases BamHI and XbaI and then purified as described in Example 1. This fragment is designated F2.

The vector pA2 (modification of pVL941 vector, discussed below) is used for the expression of the neuropeptide receptor protein using the baculovirus expression system (for review see: Summers, M. D. and Smith, G. E. 1987, A manual of methods for baculovirus vectors and insect cell culture procedures, Texas Agricultural Experimental Station Bulletin NO:1, 3 and 5555). This expression vector contains the strong polyhedrin promoter of the Autographa californica nuclear polyhidrosis virus (AcMNPV) followed by the recognition sites for the restriction endonucleases BamHI and XbaI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and XbaI and then dephosphorylated using calf intestinal phosphatase by procedures known in the art. The DNA is then isolated from a 16 agarose gel as described in Example 1. This vector DNA is designated V2.

Fragment F2 and the dephosphorylated plasmid V2 are ligated with T4 DNA ligase. DH$_5$u are then transformed and bacteria identified that contained the plasmid (pBac neuropeptide receptor) with the neuropeptide receptor gene using the enzymes BamHI and XbaI. The sequence of the cloned fragment is confirmed by DNA sequencing. 5 µg of the plasmid pBac neuropeptide receptor are co-transfected with 1.0 µg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)). 1 µg of BaculoGold™ virus DNA and 5 µg of the plasmid pBac neuropeptide receptor are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. Then the transfection mixture is added drop wise to the Sf9 insect cells (ATCC CRL 1711) seeded in a 35 mm tissue culture plate with 1 ml Grace' medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus is added to the cells and blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculoviruses is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-neuropeptide receptor at a multiplicity of infection (MOI) of 2. Six hours later the medium is removed and replaced with SF900 II medium minus methionine and cysteine (Life Technologies Inc., Gaithersburg). 42 hours later 5 µCi of $^{35}$S-methionine and 5 µCi 35S cysteine (Amersham) are added. The cells are further incubated for 16 hours before they are harvested by centrifugation and the labelled proteins visualized by SDS-PAGE and autoradiography.

EXAMPLE 4

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a nucleic acid sequence selected from the group consisting of:
   (a) a polynucleotide encoding amino acids 1–46 of SEQ ID NO:2;
   (b) a polynucleotide encoding amino acids 47–72 of SEQ ID NO:2;
   (c) a polynucleotide encoding amino acids 73–82 of SEQ ID NO:2;
   (d) a polynucleotide encoding amino acids 83–106 of SEQ ID NO:2;
   (e) a polynucleotide encoding amino acids 112–142 of SEQ ID NO:2;
   (f) a polynucleotide encoding amino acids 163–189 of SEQ ID NO:2;
   (g) a polynucleotide encoding amino acids 190–213 of SEQ ID NO:2;
   (i) a polynucleotide encoding amino acids 335–363 of SEQ ID NO:2;
   (j) a polynucleotide encoding amino acids 364–402 of SEQ ID NO:2; and
   (k) a polynucleotide encoding amino acids 364–372 of SEQ ID NO:6.

2. The isolated polynucleotide of claim 1, wherein said polynucleotide is (a).

3. The isolated polynucleotide of claim 1, wherein said polynucleotide is (b).

4. The isolated polynucleotide of claim 1, wherein said polynucleotide is (c).

5. The isolated polynucleotide of claim 1, wherein said polynucleotide is (d).

6. The isolated polynucleotide of claim 1, wherein said polynucleotide is (e).

7. The isolated polynucleotide of claim 1, wherein said polynucleotide is (f).

8. The isolated polynucleotide of claim 1, wherein said polynucleotide is (g).

9. The isolated polynucleotide of claim 1, wherein said polynucleotide is (h).

10. The isolated polynucleotide of claim 1, wherein said polynucleotide is (i).

11. The isolated polynucleotide of claim 1, wherein said polynucleotide is (j).

12. The isolated polynucleotide of claim 1, wherein said polynucleotide is (k).

13. The isolated polynucleotide of claim 1 fused to a heterologous polynucleotide.

14. The isolated polynucleotide of claim 13, wherein the heterologous polynucleotide encodes for a heterologous polypeptide.

15. The isolated polynucleotide of claim 1, wherein the polynucleotide is DNA.

16. The isolated polynucleotide of claim 1, wherein the polynucleotide is double stranded.

17. An isolated polynucleotide comprising the full complement of claim 1.

18. A vector comprising the polynucleotide of claim 1.

19. A method of producing a vector comprising inserting the isolated polynucleotide of claim 1 into a vector.

20. An isolated host cell comprising the vector of claim 18.

21. An isolated host cell comprising the polynucleotide of claim 1 operably associated with a heterologous regulatory sequence.

22. A method of producing a host cell comprising inserting the isolated polynucleotide of claim 1 into a host cell.

23. A method of producing a polypeptide comprising:
(a) culturing the isolated host cell of claim 20 or claim 21 under conditions such that said polypeptide is expressed; and
(b) recovering said polypeptide.

24. A method of screening a ligand comprising:
(a) obtaining a sample suspected of containing a ligand,
(b) contacting the sample with the isolated host cell of claim 20 or claim 21 wherein the polynucleotide has human neuropeptide receptor activity, and
(c) determining whether the ligand binds to a polypeptide expressed by the polynucleotide.

25. An isolated polynucleotide comprising a nucleic acid sequence selected from the group consisting of:
(a) a polynucleotide encoding amino acids 2–402 of SEQ ID NO:2;
(b) a polynucleotide encoding amino acids 2–369 of SEQ ID NO:4
(c) a polynucleotide encoding amino acids 2–372 of SEQ ID NO:6; and
(d) a polynucleotide encoding the protein encoded by ATCC Deposit No. 97128.

26. The isolated polynucleotide of claim 25, wherein said polynucleotide is (a).

27. The isolated polynucleotide of claim 26 fused to a heterologous polynucleotide.

28. The isolated polynucleotide of claim 27, wherein the heterologous polynucleotide encodes for a heterologous polypeptide.

29. The isolated polynucleotide of claim 26, wherein the polynucleotide is DNA.

30. The isolated polynucleotide of claim 26, wherein the polynucleotide is double stranded.

31. An isolated polynucleotide comprising the full complement of claim 26.

32. A vector comprising the polynucleotide of claim 26.

33. A method of producing a vector comprising inserting the isolated polynucleotide of claim 26 into a vector.

34. An isolated host cell comprising the vector of claim 32.

35. A isolated host cell comprising the polynucleotide of claim 26 operably associated with a heterologous regulatory sequence.

36. A method of producing a host cell comprising inserting the isolated polynucleotide of claim 26 into a host cell.

37. A method of producing a polypeptide comprising:
(a) culturing the isolated host cell of claim 34 or claim 35 under conditions such that said polypeptide is expressed; and
(b) recovering said polypeptide.

38. A method of screening a ligand comprising:
(a) obtaining a sample suspected of containing a ligand,
(b) contacting the sample with the isolated host cell of claim 34 or claim 35, wherein the polynucleotide has human neuropeptide receptor activity, and
(c) determining whether the ligand binds to a polypeptide expressed by the polynucleotide.

39. The isolated polynucleotide of claim 26, wherein said polynucleotide encodes amino acids 1–402 of SEQ ID NO:2.

40. The isolated polynucleotide of claim 39, fused to a heterologous polynucleotide.

41. The isolated polynucleotide of claim 40, wherein the heterologous polynucleotide encodes for a heterologous polypeptide.

42. The isolated polynucleotide of claim 39, wherein the polynucleotide is DNA.

43. The isolated polynucleotide of claim 39, wherein the polynucleotide is double stranded.

44. An isolated polynucleotide comprising the full complement of claim 39.

45. A vector comprising the polynucleotide of claim 39.

46. A method of producing a vector comprising inserting the isolated polynucleotide of claim 39 into a vector.

47. An isolated host cell comprising the vector of claim 45.

48. An isolated host cell comprising the polynucleotide of claim 39 operably associated with a heterologous regulatory sequence.

49. A method of producing a host cell comprising inserting the isolated polynucleotide of claim 39 into a host cell.

50. A method of producing a polypeptide comprising:
(a) culturing the isolated host cell of claim 47 or claim 48 under conditions such that said polypeptide is expressed; and
(b) recovering said polypeptide.

51. A method of screening a ligand comprising:
(a) obtaining a sample suspected of containing a ligand,
(b) contacting the sample with the isolated host cell of claim 47 or claim 48 wherein the polynucleotide has human neuropeptide receptor activity, and
(c) determining whether the ligand binds to a polypeptide expressed by the polynucleotide.

52. The isolated polynucleotide of claim 25, wherein said polynucleotide is (b).

53. The isolated polynucleotide of claim 52 fused to a heterologous polynucleotide.

54. The isolated polynucleotide of claim 53, wherein the heterologous polynucleotide encodes for a heterologous polypeptide.

55. The isolated polynucleotide of claim 52, wherein the polynucleotide is DNA.

56. The isolated polynucleotide of claim 52, wherein the polynucleotide is double stranded.

57. An isolated polynucleotide comprising the full complement of claim 52.

58. A vector comprising the polynucleotide of claim 52.

59. A method of producing a vector comprising inserting the isolated polynucleotide of claim 52 into a vector.

60. An isolated host cell comprising the vector of claim 58.

61. An isolated host cell comprising the polynucleotide of claim 52 operably associated with a heterologous regulatory sequence.

62. A method producing a host cell comprising inserting the isolated polynucleotide of claim 52 into a host cell.

63. A method of producing a polypeptide comprising:
(a) culturing the isolated host cell of claim 60 or claim 61 under conditions such that said polypeptide is expressed; and
(b) recovering said polypeptide.

64. A method of screening a ligand comprising:
(a) obtaining a sample suspected of containing a ligand,
(b) contacting the sample with the isolated host cell of claim 60 or claim 61 wherein the polynucleotide has human neuropeptide receptor activity, and (c) determining whether the ligand binds to a polypeptide expressed by the polynucleotide.

65. The isolated polynucleotide of 52, wherein said polynucleotide encodes amino acids 1–369 of SEQ ID NO:4.

66. The isolated polynucleotide of claim 65, fused to a heterologous polynucleotide.

67. The isolated polynucleotide of claim 66, wherein the heterologous polynucleotide encodes for a heterologous polypeptide.

68. The isolated polynucleotide of claim 65, wherein the polynucleotide is DNA.

69. The isolated polynucleotide of claim 65, wherein the polynucleotide is double stranded.

70. An isolated polynucleotide comprising the full complement of claim 65.

71. A vector comprising the polynucleotide of claim 65.

72. A method of producing a vector comprising inserting the isolated polynucleotide of claim 65 into a vector.

73. An isolated host cell comprising the vector of claim 71.

74. An isolated host cell comprising the polynucleotide of claim 65 operably associated with a heterologous regulatory sequence.

75. A method of producing a host cell comprising inserting the isolated polynucleotide of claim 65 into a host cell.

76. A method of producing a polypeptide comprising:
(a) culturing the isolated host cell of claim 73 or claim 74 under conditions such that said polypeptide is expressed; and
(b) recovering said polypeptide.

77. A method of screening a ligand comprising:
(a) obtaining a sample suspected of containing a ligand,
(b) contacting the sample with the isolated host cell of claim 73 or claim 74 wherein the polynucleotide has human neuropeptide receptor activity, and
(c) determining whether the ligand binds to a polypeptide expressed by the polynucleotide.

78. The isolated polynucleotide of claim 25, wherein said polynucleotide is (c).

79. The isolated polynucleotide of claim 78, fused to a heterologous polynucleotide.

80. The isolated polynucleotide of claim 79, wherein the heterologous polynucleotide encodes for a heterologous polypeptide.

81. The isolated polynucleotide of claim 78, wherein the polynucleotide is DNA.

82. The isolated polynucleotide of claim 78, wherein the polynucleotide is double stranded.

83. An isolated polynucleotide comprising the full complement of claim 78.

84. A vector comprising the polynucleotide of claim 78.

85. A method of producing a vector comprising inserting the isolated polynucleotide of claim 78 into a vector.

86. An isolated host cell comprising the vector of claim 84.

87. An isolated host cell comprising the polynucleotide of claim 78 operably associated with a heterologous regulatory sequence.

88. A method of producing a host cell comprising inserting the isolated polynucleotide of claim 78 into a host cell.

89. A method of producing a polypeptide comprising:
(a) culturing the isolated host cell of claim 86 or claim 87 under conditions such that said polypeptide is expressed; and
(b) recovering said polypeptide.

90. A method of screening a ligand comprising:
(a) obtaining a sample suspected of containing a ligand,
(b) contacting the sample with the isolated host cell of claim 86 or claim 87 wherein the polynucleotide has human neuropeptide receptor activity, and
(c) determining whether the ligand binds to a polypeptide expressed by the polynucleotide.

91. The isolated polynucleotide of claim 78, wherein said polynucleotide encodes amino acids 1–372 of SEQ ID NO:6.

92. The isolated polynucleotide of claim 91 fused to a heterologous polynucleotide.

93. The isolated polynucleotide of claim 92, wherein the heterologous polynucleotide encodes for a heterologous polypeptide.

94. The isolated polynucleotide of claim 91, wherein the polynucleotide is DNA.

95. The isolated polynucleotide of claim 91, wherein the polynucleotide is double stranded.

96. An isolated polynucleotide comprising the full complement of claim 91.

97. A vector comprising the polynucleotide of claim 91.

98. A method of producing a vector comprising inserting the isolated polynucleotide of claim 91 into a vector.

99. An isolated host cell comprising the vector of claim 97.

100. An isolated host cell comprising the polynucleotide of claim 91 operably associated with a heterologous regulatory sequence.

101. A method of producing a host cell comprising inserting the isolated polynucleotide of claim 91 into a host cell.

102. A method of producing a polypeptide comprising:
(a) culturing the isolated host cell of claim 99 or claim 100 under conditions such that said polypeptide is expressed; and
(b) recovering said polypeptide.

103. A method of screening a ligand comprising:
(a) obtaining a sample suspected of containing a ligand,
(b) contacting the sample with the isolated host cell of claim 99 or claim 100 wherein the polynucleotide has human neuropeptide receptor activity, and
(c) determining whether the ligand binds to a polypeptide expressed by the polynucleotide.

104. The isolated polynucleotide of claim 25, wherein said polynucleotide is (d).

105. The isolated polynucleotide of claim 104 fused to a heterologous polynucleotide.

106. The isolated polynucleotide of claim 105, wherein the heterologous polynucleotide encodes for a heterologous polypeptide.

107. The isolated polynucleotide of claim 104, wherein the polynucleotide is DNA.

108. The isolated polynucleotide of claim 104, wherein the polynucleotide is double stranded.

109. An isolated polynucleotide comprising the full complement of claim 104.

110. A vector comprising the polynucleotide of claim 104.

111. A method of producing a vector comprising inserting the isolated polynucleotide of claim 104 into a vector.

112. An isolated host cell comprising the vector of claim 110.

113. An isolated host cell comprising the polynucleotide of claim 104 operably associated with a heterologous regulatory sequence.

114. A method of producing a host cell comprising inserting the isolated polynucleotide of claim 104 into a host cell.

115. A method of producing a polypeptide comprising:
(a) culturing the isolated host cell of claim 112 or claim 113 under conditions such that said polypeptide is expressed; and
(b) recovering said polypeptide.

116. A method of screening a ligand comprising:
(a) obtaining a sample suspected of containing a ligand,
(b) contacting the sample with the isolated host cell of claim 112 or claim 113 wherein the polynucleotide has human neuropeptide receptor activity, and
(c) determining whether the ligand binds to a polypeptide expressed by the polynucleotide.

117. A polynucleotide encoding a polypeptide fragment selected from a group consisting of:
(a) a polypeptide fragment of SEQ ID NO:2 wherein said fragment has human neuropeptide receptor activity;
(b) a polypeptide fragment of SEQ ID NO:4 wherein said fragment has human neuropeptide receptor activity;
(c) a polypeptide fragment of SEQ ID NO:6 wherein said fragment has human neuropeptide receptor activity; and
(d) a polypeptide fragment encoded by ATCC Deposit No. 97128 wherein said fragment has human neuropeptide receptor activity.

118. The isolated polynucleotide of claim 117, wherein said polynucleotide is (a).

119. The isolated polynucleotide of claim 118 fused to a heterologous polynucleotide.

120. The isolated polynucleotide of claim 119, wherein the heterologous polynucleotide encodes for a heterologous polypeptide.

121. The isolated polynucleotide of claim 118, wherein the polynucleotide is DNA.

122. The isolated polynucleotide of claim 118, wherein the polynucleotide is double stranded.

123. An isolated polynucleotide comprising the full complement of claim 118.

124. A vector comprising the polynucleotide of claim 118.

125. A method producing a vector comprising inserting the isolated polynucleotide of claim 118 into a vector.

126. An isolated host cell comprising the vector of claim 124.

127. A isolated host cell comprising the polynucleotide of claim 118 operably associated with a heterologous regulatory sequence.

128. A method of producing a host cell comprising inserting the isolated polynucleotide of claim 118 into a host cell.

129. A method of producing a polypeptide comprising:
(a) culturing the isolated host cell of claim 126 or claim 127 under conditions such that said polypeptide is expressed; and
(b) recovering said polypeptide.

130. A method of screening a ligand comprising:
(a) obtaining a sample suspected of containing a ligand,
(b) contacting the sample with the isolated host cell of claim 126 or claim 127 wherein the polynucleotide has human neuropeptide receptor activity, and
(c) determining whether the ligand binds to a polypeptide expressed by the polynucleotide.

131. The isolated polynucleotide of claim 117, wherein said polynucleotide is (b).

132. The isolated polynucleotide of claim 131 fused to a heterologous polynucleotide.

133. The isolated polynucleotide of claim 132, wherein the heterologous polynucleotide encodes for a heterologous polypeptide.

134. The isolated polynucleotide of claim 131, wherein the polynucleotide is DNA.

135. The isolated polynucleotide of claim 131, wherein the polynucleotide is double stranded.

136. An isolated polynucleotide comprising the full complement of claim 131.

137. A vector comprising the polynucleotide of claim 131.

138. A method of producing a vector comprising inserting the isolated polynucleotide of claim 131 into a vector.

139. An isolated host cell comprising the vector of claim 137.

140. An isolated host cell comprising the polynucleotide of claim 131 operably associated with a heterologous regulatory sequence.

141. A method of producing a host cell comprising inserting the isolated polynucleotide of claim 131 into a host cell.

142. A method of producing a polypeptide comprising:
(a) culturing the isolated host cell of claim 139 or claim 140 under conditions such that said polypeptide is expressed; and
(b) recovering said polypeptide.

143. A method of screening a ligand comprising:
(a) obtaining a sample suspected of containing a ligand,
(b) contacting the sample with the isolated host cell of claim 139 or claim 140 wherein the polynucleotide has human neuropeptide receptor activity, and
(c) determining whether the ligand binds to a polypeptide expressed by the polynucleotide.

144. The isolated polynucleotide of claim 117, wherein said polynucleotide is (c).

145. The isolated polynucleotide of claim 144 fused to a heterologous polynucleotide.

146. The isolated polynucleotide of claim 145, wherein the heterologous polynucleotide encodes for a heterologous polypeptide.

147. The isolated polynucleotide of claim 144, wherein the polynucleotide is DNA.

148. The isolated polynucleotide of claim 144, wherein the polynucleotide is double stranded.

149. An isolated polynucleotide comprising the full complement of claim 144.

150. A vector comprising the polynucleotide of claim 144.

151. A method of producing a vector comprising inserting the isolated polynucleotide of claim 144 into a vector.

152. An isolated host cell comprising the vector of claim 150.

153. An isolated host cell comprising the polynucleotide of claim 144 operably associated with a heterologous regulatory sequence.

154. A method o producing a host cell comprising inserting the isolated polynucleotide of claim 144 into a host cell.

155. A method of producing a polypeptide comprising:
(a) culturing the isolated host cell of claim 152 or claim 153 under conditions such that said polypeptide is expressed; and
(b) recovering said polypeptide.

156. A method of screening a ligand comprising:
(a) obtaining a sample suspected of containing a ligand,
(b) contacting the sample with the isolated host cell of claim 152 or claim 153 wherein the polynucleotide has human neuropeptide receptor activity, and
(c) determining whether the ligand binds to a polypeptide expressed by the polynucleotide.

157. The isolated polynucleotide of claim 117, wherein said polynucleotide is (d).

158. The isolated polynucleotide of claim 157 fused to a heterologous polynucleotide.

159. The isolated polynucleotide of claim 158, wherein the heterologous polynucleotide encodes for a heterologous polypeptide.

160. The isolated polynucleotide of claim 157, wherein the polynucleotide is DNA.

161. The isolated polynucleotide of claim 157, wherein the polynucleotide is double stranded.

162. An isolated polynucleotide comprising the full complement of claim 157.

163. A vector comprising the polynucleotide of claim 157.

164. A method o producing a vector comprising inserting the isolated polynucleotide of claim 157 into a vector.

165. An isolated host cell comprising the vector of claim 163.

166. An isolated host cell comprising the polynucleotide of claim 157 operably associated with a heterologous regulatory sequence.

167. A method of producing a host cell comprising inserting the isolated polynucleotide of claim 157 into a host cell.

168. A method of producing a polypeptide comprising:
   (a) culturing the isolated host cell of claim 165 or claim 166 under conditions such that said polypeptide is expressed; and
   (b) recovering said polypeptide.

169. A method of screening a ligand comprising:
   (a) obtaining a sample suspected of containing a ligand,
   (b) contacting the sample with the isolated host cell of claim 165 or claim 166 wherein the polynucleotide has human neuropeptide receptor activity, and
   (c) determining whether the ligand binds to a polypeptide expressed by the polynucleotide.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 1209 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1209

(xi) SEQUENCE DESCRIPTION: SEQ ID NO:1:

```
ATG GAG CCC TCA GCC ACC CCA GGG GCC CAG A TG GGG GTC CCC CCT GGC      48
Met Glu Pro Ser Ala Thr Pro Gly Ala Gln M et Gly Val Pro Pro Gly
 1               5                  10                  15

AGC AGA GAG CCG TCC CCT GTG CCT CCA GAC T AT GAA GAT GAG TTT CTC      96
Ser Arg Glu Pro Ser Pro Val Pro Pro Asp T yr Glu Asp Glu Phe Leu
```

-continued

| | | |
|---|---|---|
| CGC TAT CTG TGG CGT GAT TAT CTG TAC CCA A AA CAG TAT GAG TGG GTC<br>Arg Tyr Leu Trp Arg Asp Tyr Leu Tyr Pro L ys Gln Tyr Glu Trp Val<br>35                          40                    45 | 144 |
| CTC ATC GCA GCC TAT GTG GCT GTG TTC GTC G TG GCC CTG GTG GGC AAC<br>Leu Ile Ala Ala Tyr Val Ala Val Phe Val V al Ala Leu Val Gly Asn<br>50                          55                    60 | 192 |
| ACG CTG GTC TGC CTG GCC GTG TGG CGG AAC C AC CAC ATG AGG ACA GTC<br>Thr Leu Val Cys Leu Ala Val Trp Arg Asn H is His Met Arg Thr Val<br>65                          70                    75                    80 | 240 |
| ACC AAC TAC TTC ATT GTC AAC CTG TCC CTG G CT GAC GTT CTG GTG ACT<br>Thr Asn Tyr Phe Ile Val Asn Leu Ser Leu A la Asp Val Leu Val Thr<br>                      85                    90                    95 | 288 |
| GCT ATC TGC CTG CCG GCC AGC CTG CTG GTG G AC ATC ACT GAG TCC TGG<br>Ala Ile Cys Leu Pro Ala Ser Leu Leu Val A sp Ile Thr Glu Ser Trp<br>                      100                  105                110 | 336 |
| CTG TTC GGC CAT GCC CTC TGC AAG GTC ATC C CC TAT CTA CAG GCT GTG<br>Leu Phe Gly His Ala Leu Cys Lys Val Ile P ro Tyr Leu Gln Ala Val<br>                      115                  120                125 | 384 |
| TCC GTG TCA GTG GCA GTG CTA ACT CTC AGC T TC ATC GCC CTG GAC CGC<br>Ser Val Ser Val Ala Val Leu Thr Leu Ser P he Ile Ala Leu Asp Arg<br>                      130                  135                140 | 432 |
| TGG TAT GCC ATC TGC CAC CCA CTA TTG TTC A AG AGC ACA GCC CGG CGG<br>Trp Tyr Ala Ile Cys His Pro Leu Leu Phe L ys Ser Thr Ala Arg Arg<br>145                      150                  155                160 | 480 |
| GCC CGT GGC TCC ATC CTG GGC ATC TGG GCT G TG TCG CTG GCC ATC ATG<br>Ala Arg Gly Ser Ile Leu Gly Ile Trp Ala V al Ser Leu Ala Ile Met<br>                      165                  170                175 | 528 |
| GTG CCC CAG GCT GCA GTC ATG GAA TGC AGC A GT GTG CTG CCT GAG CTA<br>Val Pro Gln Ala Ala Val Met Glu Cys Ser S er Val Leu Pro Glu Leu<br>                      180                  185                190 | 576 |
| GCC AAC CGC ACA CGG CTC TTC TCA GTC TGT G AT GAA CGC TGG GCA GAT<br>Ala Asn Arg Thr Arg Leu Phe Ser Val Cys A sp Glu Arg Trp Ala Asp<br>                      195                  200                205 | 624 |
| GAC CTC TAT CCC AAG ATC TAC CAC AGT TGC T TC TTT ATT GTC ACC TAC<br>Asp Leu Tyr Pro Lys Ile Tyr His Ser Cys P he Phe Ile Val Thr Tyr<br>210                      215                  220 | 672 |
| CTG GCC CCA CTG GGC CTC ATG GCC ATG GCC T AT TTC CAG ATA TTC CGC<br>Leu Ala Pro Leu Gly Leu Met Ala Met Ala T yr Phe Gln Ile Phe Arg<br>225                      230                  235                240 | 720 |
| AAG CTC TGG GGC CGC CAG ATC CCC GGG ACC A CC TCA GCA CTG GTG CGG<br>Lys Leu Trp Gly Arg Gln Ile Pro Gly Thr T hr Ser Ala Leu Val Arg<br>                      245                  250                255 | 768 |
| AAC TGG AAG CGC CCC TCA GAC CAG CTG GGG G AC CTG GAG CAG GGC CTG<br>Asn Trp Lys Arg Pro Ser Asp Gln Leu Gly A sp Leu Glu Gln Gly Leu<br>                      260                  265                270 | 816 |
| AGT GGA GAG CCC CAG CCC CGG GGC CGC GCC T TC CTG GCT GAA GTG AAG<br>Ser Gly Glu Pro Gln Pro Arg Gly Arg Ala P he Leu Ala Glu Val Lys<br>                      275                  280                285 | 864 |
| CAG ATG CGT GCA CGG AGG AAG ACA GCC AAG A TG CTG ATG GTG GTG CTG<br>Gln Met Arg Ala Arg Arg Lys Thr Ala Lys M et Leu Met Val Val Leu<br>                      290                  295                300 | 912 |
| CTG GTC TTC GCC CTC TGC TAC CTG CCC ATC A GC GTC CTC AAT GTC CTT<br>Leu Val Phe Ala Leu Cys Tyr Leu Pro Ile S er Val Leu Asn Val Leu<br>305                      310                  315                320 | 960 |
| AAG AGG GTG TTC GGG ATG TTC CGC CAA GCC A GT GAC CGC GAA GCT GTC<br>Lys Arg Val Phe Gly Met Phe Arg Gln Ala S er Asp Arg Glu Ala Val<br>                      325                  330                335 | 1008 |
| TAC GCC TGC TTC ACC TTC TCC CAC TGG CTG G TG TAC GCC AAC AGC GCT | 1056 |

```
Tyr Ala Cys Phe Thr Phe Ser His Trp Leu Val Tyr Ala Asn Ser Ala
        340                 345                 350

GCC AAC CCC ATC ATC TAC AAC TTC CTC AGT GGC AAA TTC CGG GAG CAG         1104
Ala Asn Pro Ile Ile Tyr Asn Phe Leu Ser Gly Lys Phe Arg Glu Gln
            355                 360                 365

TTT AAG GCT GCC TTC TCC TGC TGC CTG CCT GGC CTG GGT CCC TGC GGC         1152
Phe Lys Ala Ala Phe Ser Cys Cys Leu Pro Gly Leu Gly Pro Cys Gly
370                 375                 380

TCT CTG AAG GCC CCT AGT CCC CGC TCC TCT GCC AGC CAC AAG TCC TTG         1200
Ser Leu Lys Ala Pro Ser Pro Arg Ser Ser Ala Ser His Lys Ser Leu
385                 390                 395                 400

TCC TTG TAG                                                             1209
Ser Leu *

(2) INFORMATION FOR SEQ ID NO:2:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Pro Ser Ala Thr Pro Gly Ala Gln Met Gly Val Pro Pro Gly
1               5                   10                  15

Ser Arg Glu Pro Ser Pro Val Pro Pro Asp Tyr Glu Asp Glu Phe Leu
            20                  25                  30

Arg Tyr Leu Trp Arg Asp Tyr Leu Tyr Pro Lys Gln Tyr Glu Trp Val
        35                  40                  45

Leu Ile Ala Ala Tyr Val Ala Val Phe Val Val Ala Leu Val Gly Asn
    50                  55                  60

Thr Leu Val Cys Leu Ala Val Trp Arg Asn His His Met Arg Thr Val
65                  70                  75                  80

Thr Asn Tyr Phe Ile Val Asn Leu Ser Leu Ala Asp Val Leu Val Thr
                85                  90                  95

Ala Ile Cys Leu Pro Ala Ser Leu Leu Val Asp Ile Thr Glu Ser Trp
            100                 105                 110

Leu Phe Gly His Ala Leu Cys Lys Val Ile Pro Tyr Leu Gln Ala Val
        115                 120                 125

Ser Val Ser Val Ala Val Leu Thr Leu Ser Phe Ile Ala Leu Asp Arg
    130                 135                 140

Trp Tyr Ala Ile Cys His Pro Leu Leu Phe Lys Ser Thr Ala Arg Arg
145                 150                 155                 160

Ala Arg Gly Ser Ile Leu Gly Ile Trp Ala Val Ser Leu Ala Ile Met
                165                 170                 175

Val Pro Gln Ala Ala Val Met Glu Cys Ser Ser Val Leu Pro Glu Leu
            180                 185                 190

Ala Asn Arg Thr Arg Leu Phe Ser Val Cys Asp Glu Arg Trp Ala Asp
        195                 200                 205

Asp Leu Tyr Pro Lys Ile Tyr His Ser Cys Phe Phe Ile Val Thr Tyr
    210                 215                 220

Leu Ala Pro Leu Gly Leu Met Ala Met Ala Tyr Phe Gln Ile Phe Arg
225                 230                 235                 240

Lys Leu Trp Gly Arg Gln Ile Pro Gly Thr Thr Ser Ala Leu Val Arg
                245                 250                 255

Asn Trp Lys Arg Pro Ser Asp Gln Leu Gly Asp Leu Glu Gln Gly Leu
```

-continued

```
                        260                 265                 270
Ser Gly Glu Pro Gln Pro Arg Gly Arg Ala P he Leu Ala Glu Val Lys
            275                 280                 285

Gln Met Arg Ala Arg Arg Lys Thr Ala Lys M et Leu Met Val Val Leu
    290                 295                 300

Leu Val Phe Ala Leu Cys Tyr Leu Pro Ile S er Val Leu Asn Val Leu
305                 310                 315                 320

Lys Arg Val Phe Gly Met Phe Arg Gln Ala S er Asp Arg Glu Ala Val
                325                 330                 335

Tyr Ala Cys Phe Thr Phe Ser His Trp Leu V al Tyr Ala Asn Ser Ala
            340                 345                 350

Ala Asn Pro Ile Ile Tyr Asn Phe Leu Ser G ly Lys Phe Arg Glu Gln
            355                 360                 365

Phe Lys Ala Ala Phe Ser Cys Cys Leu Pro G ly Leu Gly Pro Cys Gly
        370                 375                 380

Ser Leu Lys Ala Pro Ser Pro Arg Ser Ser A la Ser His Lys Ser Leu
385                 390                 395                 400

Ser Leu
```

(2) INFORMATION FOR SEQ ID NO:3:

(i) SEQUENCE CHARACTERISTICS:
        (A) LENGTH: 1109 a mino acids
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1110

(xi) SEQUENCE DESCRIPTION: SEQ ID NO:3:

```
ATG GAG CCC TCA GCC ACC CCA GGG GCC CAG A TG GGG GTC CCC CCT GGC      48
Met Glu Pro Ser Ala Thr Pro Gly Ala Gln M et Gly Val Pro Pro Gly
 1               5                  10                  15

AGC AGA GAG CCG TCC CCT GTG CCT CCA GAC T AT GAA GAT GAG TTT CTC      96
Ser Arg Glu Pro Ser Pro Val Pro Pro Asp T yr Glu Asp Glu Phe Leu
            20                  25                  30

CGC TAT CTG TGG CGT GAT TAT CTG TAC CCA A AA CAG TAT GAG TGG GTC     144
Arg Tyr Leu Trp Arg Asp Tyr Leu Tyr Pro L ys Gln Tyr Glu Trp Val
        35                  40                  45

CTC ATC GCA GCC TAT GTG GCT GTG TTC GTC G TG GCC CTG GTG GGC AAC     192
Leu Ile Ala Ala Tyr Val Ala Val Phe Val V al Ala Leu Val Gly Asn
    50                  55                  60

ACG CTG GTC TGC CTG GCC GTG TGG CGG AAC C AC CAC ATG AGG ACA GTC     240
Thr Leu Val Cys Leu Ala Val Trp Arg Asn H is His Met Arg Thr Val
 65                  70                  75                  80

ACC AAC TAC TTC ATT GTC AAC CTG TCC CTG G CT GAC GTT CTG GTG ACT     288
Thr Asn Tyr Phe Ile Val Asn Leu Ser Leu A la Asp Val Leu Val Thr
                85                  90                  95

GCT ATC TGC CTG CCG GCC AGC CTG CTG GTG G AC ATC ACT GAG TCC TGG     336
Ala Ile Cys Leu Pro Ala Ser Leu Leu Val A sp Ile Thr Glu Ser Trp
            100                 105                 110

CTG TTC GGC CAT GCC CTC TGC AAG GTC ATC C CC TAT CTA CAG GCT GTG     384
Leu Phe Gly His Ala Leu Cys Lys Val Ile P ro Tyr Leu Gln Ala Val
        115                 120                 125

TCC GTG TCA GTG GCA GTG CTA ACT CTC AGC T TC ATC GCC CTG GAC CGC     432
Ser Val Ser Val Ala Val Leu Thr Leu Ser P he Ile Ala Leu Asp Arg
```

```
                130             135             140
TGG TAT GCC ATC TGC CAC CCA CTA TTG TTC A AG AGC ACA GCC CGG CGG        480
Trp Tyr Ala Ile Cys His Pro Leu Leu Phe L ys Ser Thr Ala Arg Arg
145                 150                 155                 160

GCC CGT GGC TCC ATC CTG GGC ATC TGG GCT G TG TCG CTG GCC ATC ATG        528
Ala Arg Gly Ser Ile Leu Gly Ile Trp Ala V al Ser Leu Ala Ile Met
                165                 170                 175

GTG CCC CAG GCT GCA GTC ATG GAA TGC AGC A GT GTG CTG CCT GAG CTA        576
Val Pro Gln Ala Ala Val Met Glu Cys Ser S er Val Leu Pro Glu Leu
            180                 185                 190

GCC AAC CGC ACA CGG CTC TTC TCA GTC TGT G AT GAA CGC TGG GCA GAT        624
Ala Asn Arg Thr Arg Leu Phe Ser Val Cys A sp Glu Arg Trp Ala Asp
            195                 200                 205

GAC CTC TAT CCC AAG ATC TAC CAC AGT TGC T TC TTT ATT GTC ACC TAC        672
Asp Leu Tyr Pro Lys Ile Tyr His Ser Cys P he Phe Ile Val Thr Tyr
        210                 215                 220

CTG GCC CCA CTG GGC CTC ATG GCC ATG GCC T AT TTC CAG ATA TTC CGC        720
Leu Ala Pro Leu Gly Leu Met Ala Met Ala T yr Phe Gln Ile Phe Arg
225                 230                 235                 240

AAG CTC TGG GGC CGC CAG ATC CCC GGC ACC A CC TCA GCA CTG GTG CGG        768
Lys Leu Trp Gly Arg Gln Ile Pro Gly Thr T hr Ser Ala Leu Val Arg
                245                 250                 255

AAC TGG AAG CGC CCC TCA GAC CAG CTG GGG G AC CTG GAG CAG GGC CTG        816
Asn Trp Lys Arg Pro Ser Asp Gln Leu Gly A sp Leu Glu Gln Gly Leu
            260                 265                 270

AGT GGA GAG CCC CAG CCC CGG GGC CGC GCC T TC CTG GCT GAA GTG AAG        864
Ser Gly Glu Pro Gln Pro Arg Gly Arg Ala P he Leu Ala Glu Val Lys
            275                 280                 285

CAG ATG CGT GCA CGG AGG AAG ACA GCC AAG A TG CTG ATG GTG GTG CTG        912
Gln Met Arg Ala Arg Arg Lys Thr Ala Lys M et Leu Met Val Val Leu
290                 295                 300

CTG GTC TTC GCC CTC TGC TAC CTC CCC ATC A GC GTC CTC AAT GTC CTT        960
Leu Val Phe Ala Leu Cys Tyr Leu Pro Ile S er Val Leu Asn Val Leu
305                 310                 315                 320

AAG AGG GTG TTC GGG ATG TTC CGC CAA GCC A GT GAC CGC GAA GCT GTC       1008
Lys Arg Val Phe Gly Met Phe Arg Gln Ala S er Asp Arg Glu Ala Val
                325                 330                 335

TAC GCC TGC TTC ACC TTC TCC CAC TGG CTG G TG TAC GCC AAC AGC GCT       1056
Tyr Ala Cys Phe Thr Phe Ser His Trp Leu V al Tyr Ala Asn Ser Ala
            340                 345                 350

GCC AAC CCC ATC ATC TAC AAC TTC CTC AGT G GC CTT CCC TGG AGT CTG       1104
Ala Asn Pro Ile Ile Tyr Asn Phe Leu Ser G ly Leu Pro Trp Ser Leu
            355                 360                 365

CTC TAA                                                                1110
Leu

370

(2) INFORMATION FOR SEQ ID NO:4:

(i) SEQUENCE CHARACTERISTICS:
        (A) LENGTH:  369 am ino acids
        (B) TYPE: amino acid
        (D) TOPOLOGY: linear (ii) MOLECULE TYPE: protein (xi) SEQUENCE DESCRIPTION: SEQ ID NO:4:

Met Glu Pro Ser Ala Thr Pro Gly Ala Gln M et Gly Val Pro Pro Gly
 1               5                  10                  15

Ser Arg Glu Pro Ser Pro Val Pro Pro Asp T yr Glu Asp Glu Phe Leu
```

```
            20                  25                  30
Arg Tyr Leu Trp Arg Asp Tyr Leu Tyr Pro Lys Gln Tyr Glu Trp Val
         35                  40                  45
Leu Ile Ala Ala Tyr Val Ala Val Phe Val Val Ala Leu Val Gly Asn
     50                  55                  60
Thr Leu Val Cys Leu Ala Val Trp Arg Asn His His Met Arg Thr Val
 65                  70                  75                  80
Thr Asn Tyr Phe Ile Val Asn Leu Ser Leu Ala Asp Val Leu Val Thr
                 85                  90                  95
Ala Ile Cys Leu Pro Ala Ser Leu Leu Val Asp Ile Thr Glu Ser Trp
                100                 105                 110
Leu Phe Gly His Ala Leu Cys Lys Val Ile Pro Tyr Leu Gln Ala Val
            115                 120                 125
Ser Val Ser Val Ala Val Leu Thr Leu Ser Phe Ile Ala Leu Asp Arg
        130                 135                 140
Trp Tyr Ala Ile Cys His Pro Leu Leu Phe Lys Ser Thr Ala Arg Arg
145                 150                 155                 160
Ala Arg Gly Ser Ile Leu Gly Ile Trp Ala Val Ser Leu Ala Ile Met
                165                 170                 175
Val Pro Gln Ala Ala Val Met Glu Cys Ser Ser Val Leu Pro Glu Leu
            180                 185                 190
Ala Asn Arg Thr Arg Leu Phe Ser Val Cys Asp Glu Arg Trp Ala Asp
        195                 200                 205
Asp Leu Tyr Pro Lys Ile Tyr His Ser Cys Phe Phe Ile Val Thr Tyr
    210                 215                 220
Leu Ala Pro Leu Gly Leu Met Ala Met Ala Tyr Phe Gln Ile Phe Arg
225                 230                 235                 240
Lys Leu Trp Gly Arg Gln Ile Pro Gly Thr Thr Ser Ala Leu Val Arg
                245                 250                 255
Asn Trp Lys Arg Pro Ser Asp Gln Leu Gly Asp Leu Glu Gln Gly Leu
            260                 265                 270
Ser Gly Glu Pro Gln Pro Arg Gly Arg Ala Phe Leu Ala Glu Val Lys
        275                 280                 285
Gln Met Arg Ala Arg Arg Lys Thr Ala Lys Met Leu Met Val Val Leu
    290                 295                 300
Leu Val Phe Ala Leu Cys Tyr Leu Pro Ile Ser Val Leu Asn Val Leu
305                 310                 315                 320
Lys Arg Val Phe Gly Met Phe Arg Gln Ala Ser Asp Arg Glu Ala Val
                325                 330                 335
Tyr Ala Cys Phe Thr Phe Ser His Trp Leu Val Tyr Ala Asn Ser Ala
            340                 345                 350
Ala Asn Pro Ile Ile Tyr Asn Phe Leu Ser Gly Leu Pro Trp Ser Leu
        355                 360                 365
Leu
370

(2) INFORMATION FOR SEQ ID NO:5:

(i) SEQUENCE CHARACTERISTICS:
        (A) LENGTH: 1115 amino acids
        (B) TYPE: nucleic acid
        (C) STRANDEDNESS: single
        (D) TOPOLOGY: linear (ii) MOLECULE TYPE: DNA (genomic)
```

(ix) FEATURE:
      (A) NAME/KEY: CDS
      (B) LOCATION: 1..1116

(xi) SEQUENCE DESCRIPTION: SEQ ID NO:5:

| | | | | | | | | | | | | | | | | |
|---|---|---|---|---|---|---|---|---|---|---|---|---|---|---|---|---|
| ATG | GAG | CCC | TCA | GCC | ACC | CCA | GGG | GCC | CAG | A TG | GGG | GTC | CCC | CCT | GGC | 48 |
| Met | Glu | Pro | Ser | Ala | Thr | Pro | Gly | Ala | Gln | M et | Gly | Val | Pro | Pro | Gly | |
| 1 | | | | 5 | | | | | 10 | | | | | 15 | | |
| AGC | AGA | GAC | CCC | TCC | CCT | GTG | CCT | CCA | GAC | T AT | GAA | GAT | GAG | TTT | CTC | 96 |
| Ser | Arg | Asp | Pro | Ser | Pro | Val | Pro | Pro | Asp | T yr | Glu | Asp | Glu | Phe | Leu | |
| | | | 20 | | | | | 25 | | | | | 30 | | | |
| CGC | TAT | CTG | TGG | CGT | GAT | TAT | CTG | TAC | CCA | A AA | CAG | TAT | GAG | TGG | GTC | 144 |
| Arg | Tyr | Leu | Trp | Arg | Asp | Tyr | Leu | Tyr | Pro | L ys | Gln | Tyr | Glu | Trp | Val | |
| | | 35 | | | | | 40 | | | | | 45 | | | | |
| CTC | ATC | GCA | GCC | TAT | GTG | GCT | GTG | TTC | GTC | G TG | GCC | CTG | GTG | GGC | AAC | 192 |
| Leu | Ile | Ala | Ala | Tyr | Val | Ala | Val | Phe | Val | V al | Ala | Leu | Val | Gly | Asn | |
| 50 | | | | | 55 | | | | | 60 | | | | | | |
| ACG | CTG | GTC | TGC | CTG | GCC | GTG | TGG | CGG | AAC | C AC | CAC | ATG | AGG | ACA | GTC | 240 |
| Thr | Leu | Val | Cys | Leu | Ala | Val | Trp | Arg | Asn | H is | His | Met | Arg | Thr | Val | |
| 65 | | | | 70 | | | | | 75 | | | | | 80 | | |
| ACC | AAC | TAC | TTC | ATT | GTC | AAC | CTG | TCC | CTG | G CT | GAC | GTT | CTG | GTG | ACT | 288 |
| Thr | Asn | Tyr | Phe | Ile | Val | Asn | Leu | Ser | Leu | A la | Asp | Val | Leu | Val | Thr | |
| | | | | 85 | | | | | 90 | | | | | 95 | | |
| GCT | ATC | TGC | CTG | CCG | GCC | AGC | CTG | CTG | GTG | G AC | ATC | ACT | GAG | TCC | TGG | 336 |
| Ala | Ile | Cys | Leu | Pro | Ala | Ser | Leu | Leu | Val | A sp | Ile | Thr | Glu | Ser | Trp | |
| | | | 100 | | | | | 105 | | | | | 110 | | | |
| CTG | TTC | GGC | CAT | GCC | CTC | TGC | AAG | GTC | ATC | C CC | TAT | CTA | CAG | GCT | GTG | 384 |
| Leu | Phe | Gly | His | Ala | Leu | Cys | Lys | Val | Ile | P ro | Tyr | Leu | Gln | Ala | Val | |
| | | 115 | | | | | 120 | | | | | 125 | | | | |
| TCC | GTG | TCA | GTG | GCA | GTG | CTA | ACT | CTC | AGC | T TC | ATC | GCC | CTG | GAC | CGC | 432 |
| Ser | Val | Ser | Val | Ala | Val | Leu | Thr | Leu | Ser | P he | Ile | Ala | Leu | Asp | Arg | |
| 130 | | | | | 135 | | | | | 140 | | | | | | |
| TGG | TAT | GCC | ATC | TGC | CAC | CCA | CTA | TTG | TTC | A AG | AGC | ACA | GCC | CGG | CGG | 480 |
| Trp | Tyr | Ala | Ile | Cys | His | Pro | Leu | Leu | Phe | L ys | Ser | Thr | Ala | Arg | Arg | |
| 145 | | | | 150 | | | | | 155 | | | | | 160 | | |
| GCC | CGT | GGC | TCC | ATC | CTG | GGC | ATC | TGG | GCT | G TG | TCG | CTG | GCC | ATC | ATG | 528 |
| Ala | Arg | Gly | Ser | Ile | Leu | Gly | Ile | Trp | Ala | V al | Ser | Leu | Ala | Ile | Met | |
| | | | | 165 | | | | | 170 | | | | | 175 | | |
| GTG | CCC | CAG | GCT | GCA | GTC | ATG | GAA | TGC | AGC | A GT | GTG | CTG | CCT | GAG | CTA | 576 |
| Val | Pro | Gln | Ala | Ala | Val | Met | Glu | Cys | Ser | S er | Val | Leu | Pro | Glu | Leu | |
| | | | 180 | | | | | 185 | | | | | 190 | | | |
| GCC | AAC | CGC | ACA | CGG | CTC | TTC | TCA | GTC | TGT | G AT | GAA | CGC | TGG | GCA | GAT | 624 |
| Ala | Asn | Arg | Thr | Arg | Leu | Phe | Ser | Val | Cys | A sp | Glu | Arg | Trp | Ala | Asp | |
| | | 195 | | | | | 200 | | | | | 205 | | | | |
| GAC | CTC | TAT | CCC | AAG | ATC | TAC | CAC | AGT | TGC | T TC | TTT | ATT | GTC | ACC | TAC | 672 |
| Asp | Leu | Tyr | Pro | Lys | Ile | Tyr | His | Ser | Cys | P he | Phe | Ile | Val | Thr | Tyr | |
| | 210 | | | | | 215 | | | | | 220 | | | | | |
| CTG | GCC | CCA | CTG | GGC | CTC | ATG | GCC | ATG | GCC | T AT | TTC | CAG | ATA | TTC | CGC | 720 |
| Leu | Ala | Pro | Leu | Gly | Leu | Met | Ala | Met | Ala | T yr | Phe | Gln | Ile | Phe | Arg | |
| 225 | | | | | 230 | | | | | 235 | | | | | 240 | |
| AAG | CTC | TGG | GGC | CGC | CAG | ATC | CCC | GGC | ACC | A CC | TCA | GCA | CTG | GTG | CGG | 768 |
| Lys | Leu | Trp | Gly | Arg | Gln | Ile | Pro | Gly | Thr | T hr | Ser | Ala | Leu | Val | Arg | |
| | | | | 245 | | | | | 250 | | | | | 255 | | |
| AAC | TGG | AAG | CGC | CCC | TCA | GAC | CAG | CTG | GGG | G AC | CTG | GAG | CAG | GGC | CTG | 816 |
| Asn | Trp | Lys | Arg | Pro | Ser | Asp | Gln | Leu | Gly | A sp | Leu | Glu | Gln | Gly | Leu | |
| | | | 260 | | | | | 265 | | | | | 270 | | | |
| AGT | GGA | GAG | CCC | CAG | CCC | CGG | GGC | CGC | GCC | T TC | CTG | GCT | GAA | GTG | AAG | 864 |
| Ser | Gly | Glu | Pro | Gln | Pro | Arg | Gly | Arg | Ala | P he | Leu | Ala | Glu | Val | Lys | |
| | | 275 | | | | | 280 | | | | | 285 | | | | |

```
CAG ATG CGT GCA CGG AGG AAG ACA GCC AAG A TG CTG ATG GTG GTG CTG      912
Gln Met Arg Ala Arg Arg Lys Thr Ala Lys M et Leu Met Val Val Leu
    290                 295                 300

CTG GTC TTC GCC CTC TGC TAC CTG CCC ATC A GC GTC CTC AAT GTC CTT      960
Leu Val Phe Ala Leu Cys Tyr Leu Pro Ile S er Val Leu Asn Val Leu
305                 310                 315                 320

AAG AGG GTG TTC GGG ATG TTC CGC CAA GCC A GT GAC CGC GAA GCT GTC     1008
Lys Arg Val Phe Gly Met Phe Arg Gln Ala S er Asp Arg Glu Ala Val
                325                 330                 335

TAC GCC TGC TTC ACC TTC TCC CAC TGG CTG G TG TAC GCC AAC AGC GCT     1056
Tyr Ala Cys Phe Thr Phe Ser His Trp Leu V al Tyr Ala Asn Ser Ala
                340                 345                 350

GCC AAC CCC ATC ATC TAC AAC TTC CTC AGT G GA TGT AAA GAG AAG AGT     1104
Ala Asn Pro Ile Ile Tyr Asn Phe Leu Ser G ly Cys Lys Glu Lys Ser
                355                 360                 365

CTA GTT CTG TCC                                                      1116
Leu Val Leu Ser
    370
```

(2) INFORMATION FOR SEQ ID NO:6:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:6:

```
Met Glu Pro Ser Ala Thr Pro Gly Ala Gln M et Gly Val Pro Pro Gly
 1               5                  10                  15

Ser Arg Asp Pro Ser Pro Val Pro Pro Asp T yr Glu Asp Glu Phe Leu
                20                  25                  30

Arg Tyr Leu Trp Arg Asp Tyr Leu Tyr Pro L ys Gln Tyr Glu Trp Val
            35                  40                  45

Leu Ile Ala Ala Tyr Val Ala Val Phe Val V al Ala Leu Val Gly Asn
        50                  55                  60

Thr Leu Val Cys Leu Ala Val Trp Arg Asn H is His Met Arg Thr Val
65                  70                  75                  80

Thr Asn Tyr Phe Ile Val Asn Leu Ser Leu A la Asp Val Leu Val Thr
                85                  90                  95

Ala Ile Cys Leu Pro Ala Ser Leu Leu Val A sp Ile Thr Glu Ser Trp
                100                 105                 110

Leu Phe Gly His Ala Leu Cys Lys Val Ile P ro Tyr Leu Gln Ala Val
            115                 120                 125

Ser Val Ser Val Ala Val Leu Thr Leu Ser P he Ile Ala Leu Asp Arg
        130                 135                 140

Trp Tyr Ala Ile Cys His Pro Leu Leu Phe L ys Ser Thr Ala Arg Arg
145                 150                 155                 160

Ala Arg Gly Ser Ile Leu Gly Ile Trp Ala V al Ser Leu Ala Ile Met
                165                 170                 175

Val Pro Gln Ala Ala Val Met Glu Cys Ser S er Val Leu Pro Glu Leu
                180                 185                 190

Ala Asn Arg Thr Arg Leu Phe Ser Val Cys A sp Glu Arg Trp Ala Asp
            195                 200                 205

Asp Leu Tyr Pro Lys Ile Tyr His Ser Cys P he Phe Ile Val Thr Tyr
        210                 215                 220

Leu Ala Pro Leu Gly Leu Met Ala Met Ala T yr Phe Gln Ile Phe Arg
```

-continued

```
            225                 230                 235                 240
Lys Leu Trp Gly Arg Gln Ile Pro Gly Thr T hr Ser Ala Leu Val Arg
                245                 250                 255
Asn Trp Lys Arg Pro Ser Asp Gln Leu Gly A sp Leu Glu Gln Gly Leu
                260                 265                 270
Ser Gly Glu Pro Gln Pro Arg Gly Arg Ala P he Leu Ala Glu Val Lys
            275                 280                 285
Gln Met Arg Ala Arg Arg Lys Thr Ala Lys M et Leu Met Val Val Leu
            290                 295                 300
Leu Val Phe Ala Leu Cys Tyr Leu Pro Ile S er Val Leu Asn Val Leu
305                 310                 315                 320
Lys Arg Val Phe Gly Met Phe Arg Gln Ala S er Asp Arg Glu Ala Val
                325                 330                 335
Tyr Ala Cys Phe Thr Phe Ser His Trp Leu V al Tyr Ala Asn Ser Ala
                340                 345                 350
Ala Asn Pro Ile Ile Tyr Asn Phe Leu Ser G ly Cys Lys Glu Lys Ser
            355                 360                 365
Leu Val Leu Ser
    370
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CACTAAAGCT TAATGGAGCC CTCAGCCACC                              30

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ACAAGTCCTT GTCCTTCTAG AGGGC                                  25

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CCTAGGATGC CCCTCTGCTG CAGCGG                                26

(2) INFORMATION FOR SEQ ID NO:10:

(i) SEQUENCE CHARACTERISTICS:
        (A) LENGTH: 25 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

ACAAGTCCTT GTCCTTCTAG AGGGC                                    25

(2) INFORMATION FOR SEQ ID NO:11:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

CGGGATCCGC CATCATGGAG CCCTCAGCCA CC                             32

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

ACAAGTCCTT GTCCTTCTAG AGGGC                                    25
```